(12) United States Patent
Kiesel et al.

(10) Patent No.: US 7,248,361 B2
(45) Date of Patent: Jul. 24, 2007

(54) FLUORESCENCE READER BASED ON ANTI-RESONANT WAVEGUIDE EXCITATION

(75) Inventors: Peter Kiesel, Palo Alto, CA (US); Oliver Wolst, Nürtingen (DE); Michael Kneissl, Berlin (DE); Huangpin Ben Hsieh, Mountain View, CA (US); Oliver Schmidt, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/315,797

(22) Filed: Dec. 22, 2005

(65) Prior Publication Data

US 2007/0146701 A1 Jun. 28, 2007

(51) Int. Cl.
  *G01N 21/64* (2006.01)
(52) U.S. Cl. .................................. 356/318; 250/458.1
(58) Field of Classification Search ................ 356/317, 356/318; 250/458.1
  See application file for complete search history.

(56) References Cited

U.S. PATENT DOCUMENTS

| 6,577,780 | B2 | 6/2003 | Lockhart |
| 6,603,548 | B2 | 8/2003 | Church et al. |
| 2004/0022685 | A1* | 2/2004 | Singh et al. ............. 422/82.08 |
| 2004/0252957 | A1* | 12/2004 | Schmidt et al. ............. 385/131 |
| 2006/0092413 | A1* | 5/2006 | Kiesel et al. ............... 356/301 |

FOREIGN PATENT DOCUMENTS

EP   1653217 A1   5/2006

OTHER PUBLICATIONS

R. Bernini et al., "Planar Antiresonant Reflecting Optical Waveguides as Sensors for Liquid Substances", *IEEE* 2002, 0-7802-7454, 5 pgs.
EP Search Report, Application No. 06126357.0-2204, Dated Apr. 23, 2007, Examiner Ricarda Hoogen, Munich, Germany.
Singh K. et al., "Analysis of Cellular Structure by Light Scattering Measurements in a New Cytometer Design Based on a Liquid-Core Waveguide", *IEE Proc. Nanbiotechnology*, vol. 151, No. 1, Feb. 2004, pp. 10-16, XP006021506.
Schmidt, H. et al., "Inegrated ARROW Waveguides for Gas/Liquid Sensing", *Proc. SPIE*, vol. 5515, Oct. 2004, pp. 67-80, XP002427238.
Schmidt, et al., "Guiding Light in Fluids", *Applied Physics Letters*, vol. 88, Apr. 14, 2006, pp. 151109-1-151109-3, XP012081032.

* cited by examiner

*Primary Examiner*—F. L. Evans
(74) *Attorney, Agent, or Firm*—Fay Sharpe LLP

(57) ABSTRACT

A sample detection system including an anti-resonant waveguide, including a sample having a first index of refraction, a top layer and a substrate surrounding the sample, where the top layer has a second index of refraction, and the substrate has a third index of refraction. The second index of refraction, and the third index of refraction are both greater than the first index of refraction. A detection device of the system includes a low power light source used to direct light into the sample and generate an anti-resonant optical mode in the sample, and an analyzing system to detect the interaction of the light propagating in the sample.

22 Claims, 19 Drawing Sheets

| Refractive Index of Analyt n | Angle γ' (degrees) | Angle γ" (degrees) |
|---|---|---|
| 1.00 | 48.2 | – |
| 1.05 | 45.6 | – |
| 1.10 | 42.8 | – |
| 1.15 | 39.9 | 74.4 |
| 1.20 | 36.9 | 64.2 |
| 1.25 | 33.6 | 56.0 |
| 1.30 | 29.9 | 48.4 |
| 1.35 | 25.8 | 40.8 |

FLUORESCENCE READER BASED ON ANTI-RESONANT WAVEGUIDE EXCITATION

RELATED APPLICATIONS

U.S. application Ser. No. 10/976,434, filed Oct. 29, 2004, entitled "Anti-Resonant Waveguide Sensors", is a related application, the entire specification of which is incorporated herein by reference.

BACKGROUND

In the last several years many different approaches for automated detection of biological materials have been proposed and developed. These commonly are biosensors and biochip readers which often use live organisms or biological molecules, such as antibodies, nucleic acids (e.g., DNA chips), or enzymes as biological recognition elements to specifically bind target analytes. The specific binding of the target can be monitored by a recognition signal.

One of the most sensitive detection techniques available today is based on fluorescence excitation of dye-labeled targets. Current detection devices mostly fall into one of two categories, the first employs a white light source (usually a high power arc lamp) with CCD detector, and the second using laser excitation with photomultiplier tube (PMT) light collection in combination with a scanning technique. To meet the detection demands, a fluorescent scanner usually has a sensitivity of detecting at least 2-5 fluorphores per $\mu m^2$; a resolution of 10 µm (pixel size) or better; and has a dynamic range of 5 orders of magnitude. Moreover, it needs to perform scanning of one slide in reasonable amount of time, typically five minutes or less per fluorescence channel. Problems with systems employing a white light source include the need of expensive filters and the short lifetime of arc lamp, which can be costly; while the approach using lasers is not practical for multicolor exaction due to the high cost of multiple lasers. Both types of scanners are costly and large enough to take up a substantial portion of a workbench.

A common disadvantage of all fluorescence based reading is the relatively inefficient use of the excitation light, due to the limited interaction with the fluorescence molecules. This increases the demand on the excitation source as well as on the detection system because unused excitation light is transmitted, scattered or absorbed elsewhere, decreasing the operational efficiency of the system and increasing background noise.

In order to improve the interaction, fluorescence readers employing optical waveguides have been proposed. A general disadvantage of conventional waveguide approaches is that the substance itself (e.g., liquid, which contains the molecules of interest) are not used as an optical waveguide, since the refractive index is lower than the index of the surrounding material (e.g., glass polymer, PDMS). Therefore, conventional optical waveguides typically provide only a weak interaction via evanescent waves with the target molecules, which are specifically bound to the waveguide surface. Existing waveguides also do not efficiently maintain light in the waveguide due to enhanced light scattering if the layer bound to the surface is inhomogeneous.

Thus, due to the required sensitivity of detection, and the inefficiency in the fluorescence excitation of existing systems, high powered light sources are necessary in order to obtain a sufficient amount of emitted fluorescing light. Such high powered light sources take up large amounts of physical space, require large amounts of energy to operate, and have a comparatively short life span requiring removal, replacement, and oftentimes realignment of lamp.

It is to be understood that fluorescent microscopes, as well as other detectors which employ fluorescence concepts, have the same issues regarding effective illumination and light collection from a sample and therefore face the same challenges as discussed above.

SUMMARY

A sample detection system employing an anti-resonant waveguide, having a sample with a first index of refraction, and a top layer and substrate surrounding the sample, where the top layer has a second index of refraction, and the substrate has a third index of refraction. The second index of refraction, and the third index of refraction are both greater than the first index of refraction. A detection device of the system includes a low power light source used to direct light into the sample and generate an anti-resonant optical mode in the sample, and an analyzing system to detect the interaction of the light propagating in the sample.

DETAILED DESCRIPTION

Improved compact sensors that enhance interaction between light and target analytes in a sample are described. Light from a comparatively low power light source, such as but not limited to a Light Emitting Diode (LED), Laser Diode (LD) or Superluminescent Light Emitting Diode (SLED), is coupled into a sample. It is to be appreciated that while the foregoing mentions light sources as being one of LEDs, LDs or SLEDs, a conventional higher power light source can also be used in connection with anti-resonant waveguide coupling. However, since the anti-resonant waveguide approach enhances the light target interaction anti-resonant waveguide coupling also works with the mentioned low power light sources such as LEDs, LDs and SLEDs.

Figure 1:
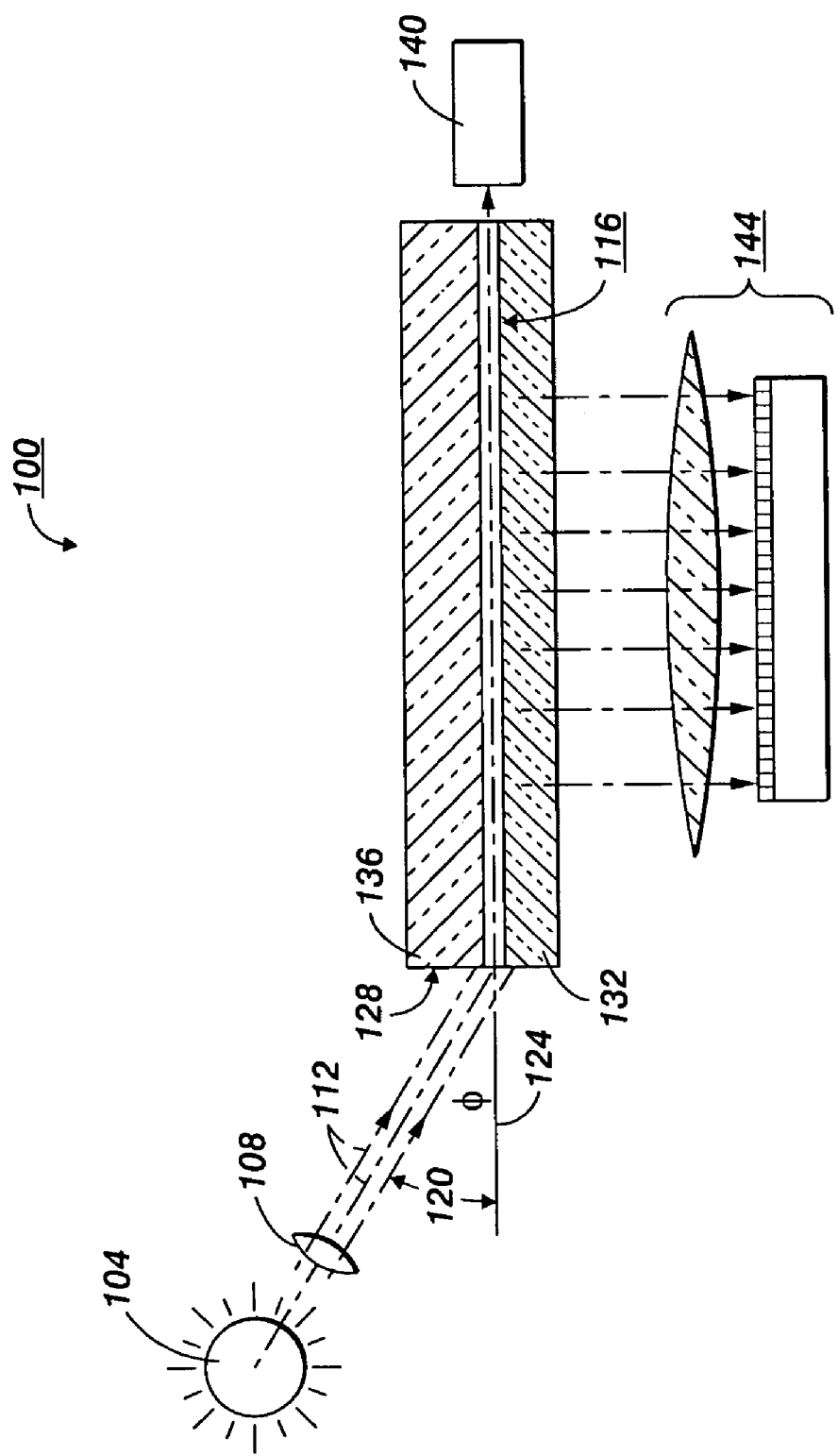
FIG. 1 shows a side sectional overview of an analysis system.

By controlling the angle of light entry into the sample, anti-resonant waveguide modes are generated. The anti-resonant modes allow the sample itself to serve as an optical waveguide resulting in increased interaction between the target molecules and the light. A light retention component acts to maintain the light within the waveguide to further improve the efficiency of the system FIG. 1 shows a side view of one embodiment of optical sensing system 100. In FIG. 1, a light source 104 and/or a lens system 108 directs a light beam 112 into a sample 116. Depending on the test being conducted, light in light beam 112 may be of coherent or incoherent. When coherent light is used, light source 104 is typically a laser. In other cases white light or light emitting diodes may be used.

Light beam 112 enters sample 116 at an angle of incidence 120. As used herein, reference to the word "light", "light beam" and "optical" is should be broadly interpreted to include a broad range of frequencies including ultraviolet, visible, infrared, and far infrared radiation as well as terahertz radiation. As used herein, the angle of incidence is the angle with respect to a normal 124 of the surface 128. The angle of incidence is carefully selected such that an anti-resonant guided optical wave (ARGOW) or mode of light can be set up within sample 116.

Sample 116 is typically a thin film of liquid carrying the target analyte (e.g., biological molecules) to be analyzed. Sample 116 may also be a gas or an aerosol carrying the analyte to be analyzed. If the sample is a gas or aerosol, sealing materials around the perimeter of the chamber containing the sample keeps the gas between substrate 132 and covering layer 136. Sample 116 thickness is usually kept larger than the wavelength of light being used to analyze the sample.

Substrate 132 and covering layer 136 border sample 116 sides. Substrate 132 and covering layer 136 are typically made from a transparent material such as glass. In one embodiment, glass slides are used for substrate 132 and covering layer 136. The index of refraction of the substrate and covering layer are slightly higher than that of the sample 116 to facilitate generation of an anti-resonant wave in sample 116. An example index of refraction of substrate 132 and covering layer 136 might be between 1.4 and 1.8 while the index of refraction of a liquid sample 116 might be between 1.2 and 1.4 although as will be explained, a wide range of other indices are also possible.

The actual conditions used to create an anti-resonant guided optical wave (ARGOW) propagating through a sample sandwiched between two higher index materials may be found by computing the Eigensolutions of the Helmholtz equation for a plane wave propagating along a slab waveguide structure. A general Helmholtz equation for the electric field E is given by:

$$(\nabla^2 + |\vec{k}|^2)E = 0; \quad |\vec{k}| = |\vec{k}_0| \cdot n \quad \text{(Eq.1)}$$

Assuming a plane wave that propagates along a x-direction within a slab waveguide structure, and confining the wave with respect to the z-orientation results in the following solution to the Helmholtz equation:

$$E = \tilde{E}(z) \cdot e^{i(k_x x - \omega t)}; \quad \frac{\partial E}{\partial y} = 0 \quad \text{(Eq. 2)}$$

where E denotes the electric field, $\tilde{E}(z)$ its z-dependence, $k_x$ the x-component of the wavevector. $\vec{k}_0$ is the lights vacuum wavevector and n the materials refractive index.

In this case the Helmholtz equation reduces to:

$$\left(\frac{\partial^2 E}{\partial z^2} + k_0^2 \cdot n^2(z)\right)\tilde{E}(z) = K_x^2(z) \cdot \tilde{E}(z). \quad \text{(Eq. 3)}$$

The Eigensolutions $\tilde{E}(z)$ can be characterized by $k_x$, or for convenience by a so called effective refractive index $n_{eff}$ defined as:

$$n_{eff} \equiv \frac{k_x}{|\vec{k}_0|} \quad \text{(Eq. 4)}$$

In the previously described slab index guided waveguide structure, the equations above can be numerically solved resulting in a large number of Eigensolutions $\tilde{E}(z)$. These Eigensolutions are called-optical modes. Equations 3 and equation 4 also enable computation of the respective refractive indices $n_{eff}$ and modal confinement factors $\Gamma$ of these modes.

Figure 6:
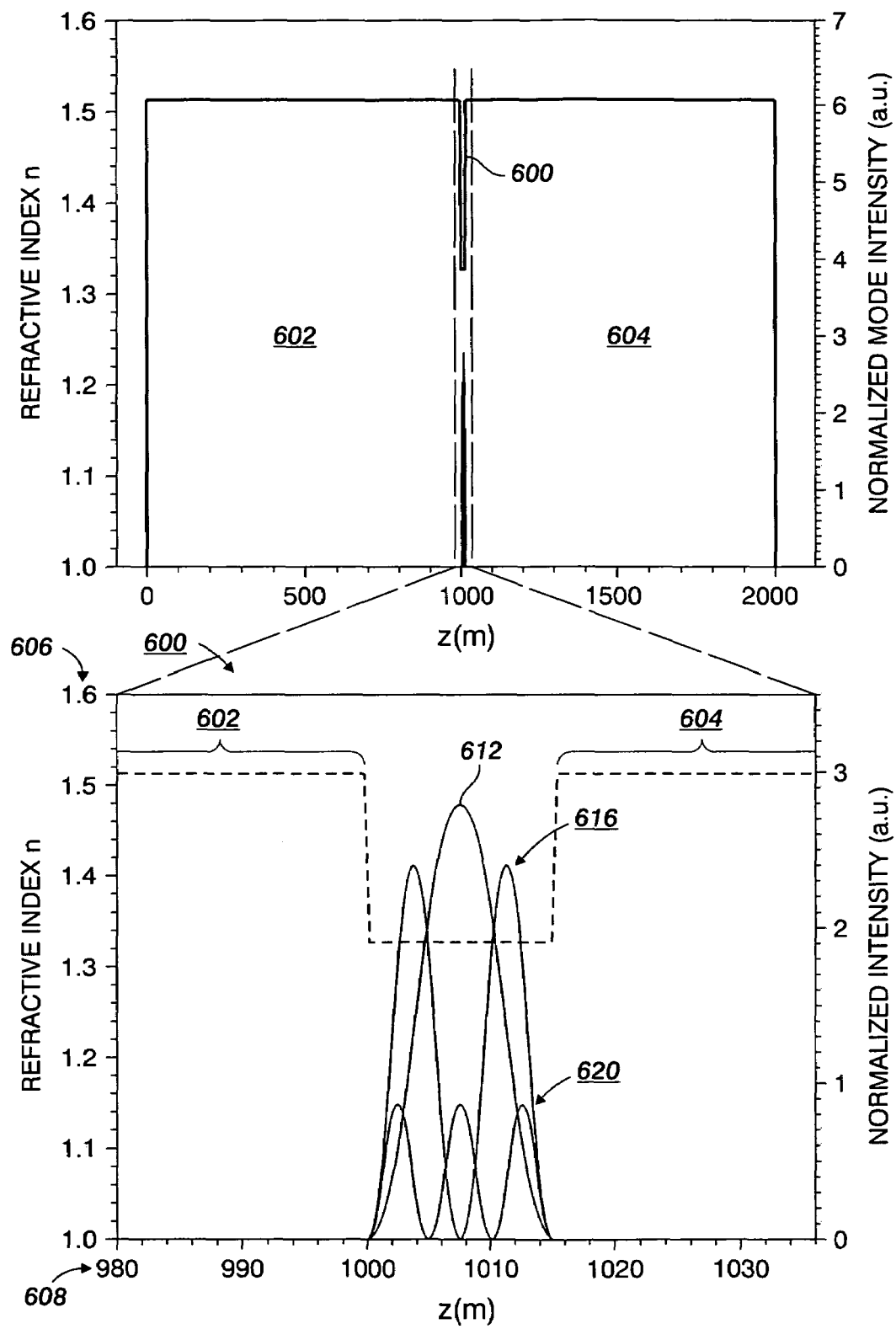
FIG. 6 shows an intensity profile of various anti-resonant modes in an example analyte cross section.

FIG. 6 shows examples of optical modes. In FIG. 6, anti-resonant intensity patterns 612, 616, 620 are plotted across a cross section of a liquid sample 600 placed between glass plates 602, 604. Typical indexes of refraction across the sample are provided along y axis 606. A distance along sample 600 is provided on x axis 608. An example first optical mode is shown by normalized intensity pattern 612, a second optical mode is shown by normalized intensity pattern 616 and a third optical mode is shown by normalized intensity pattern 620.

A confinement factor $\Gamma$ corresponds to the fraction of the light intensity confined in the waveguide core. For maximum interaction between target molecules in the sample and the light beam, the sample or analyte itself serves as the waveguide core. The core is surrounded by a cladding layer, typically the portion of the medium immediately adjacent to the sample. In future references to the cladding, the "cladding layer" shall refer to a portion of the medium that lies immediately on either side of the sample. The thickness of the cladding layer can be chosen within a wide range but the typical thickness is a several wavelengths of the light propagating in the medium.

In the case of "anti-resonant" waveguides, herein defined to be a waveguide in which the core has a lower refractive index than the cladding layer, a number of optical modes with reasonably large confinement factors, up to and past 90%, can be found. These modes (or Eigensolutions) are characterized by effective refractive indices $n_{eff}$ close to (typically slightly smaller than) the refractive index n of the core layer material. When the core thickness is large compared with the wavelength of propagating light, the $n_{eff}$ of these modes of interest, approaches the refractive index of the core n.

$$d_{core} >> \lambda \Rightarrow n_{eff} \approx n \quad \text{(Eq.5)}$$

Figures 2, 3:
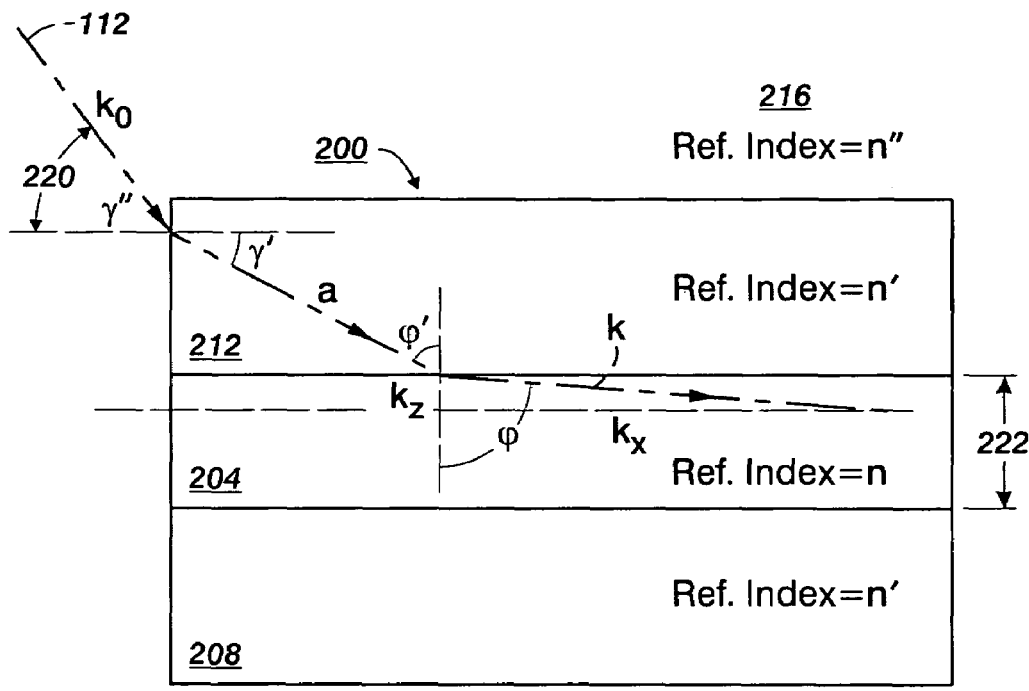
FIG. 2 shows an expanded side sectional view of a waveguide receiving an input light beam with a target-containing sample as a core.
FIG. 3 is a table showing example incidence angles for different analytes surrounded by a glass cladding.

Each Eigenmode can be excited by directing a beam of light at the waveguide at a specific angle of incidence. The angle of incidence corresponds to the effective refractive index $n_{eff}$. FIG. 2 shows one geometry of a slab waveguide 200 where the refractive index of the analyte 204 is n, the refractive index of substrate 208 and cover layer 212 are n' and the refractive index of the surroundings 216 is n". The optimum angle of incidence $\gamma(n_{eff})$ 220 for the structure of FIG. 2 may be derived as follows:

$$\sin(\varphi) = \frac{k_x}{k} = \frac{n_{eff}}{n}; \quad \text{(Eq. 6)}$$

$$\sin(\varphi') = \frac{n}{n'}\sin(\varphi) = \frac{n_{eff}}{n'};$$

$$\cos(\gamma') = \cos(90° - \varphi') = \sin(\varphi');$$

$$\gamma' = \arccos\left(\frac{n_{eff}}{n'}\right);$$

$$\sin\gamma'' = \frac{n'}{n''}\sin\gamma';$$

$$\gamma'' = \arcsin\left(\frac{n'}{n''}\arccos\left(\frac{n_{eff}}{n'}\right)\right);$$

When analyte 204 thickness 220 (typically waveguide core diameter $d_{core} \approx 10 \ldots 100$ μm) is large compared with the wavelength of the incident light ($\lambda = 0.3 \ldots 2$ μm) the approximation of (Eq.5) is acceptable. Using the equation 4 approximation allows substitution of analyte refractive index n for effective refractive index $n_{eff}$. The substitution results in an angle of incident that depends only on the refractive indices of the analyte, the core layer and the outside world:

$$\gamma'' = \arcsin\left(\frac{n'}{n''}\arccos\left(\frac{n}{n'}\right)\right); \quad \text{(Eq.7)}$$

An example of a typical set of refractive indices might be an analyte of water with an n=1.34, a glass cladding layer with an n'=1.5 and an air or vacuum surrounding with n"=1. Using a glass cladding in an air surrounding for an example, the table in FIG. 3 lists appropriate angles of incident γ" in order to generate an ARGOW mode based on the sample or analyte refractive indexes.

Figure 4:
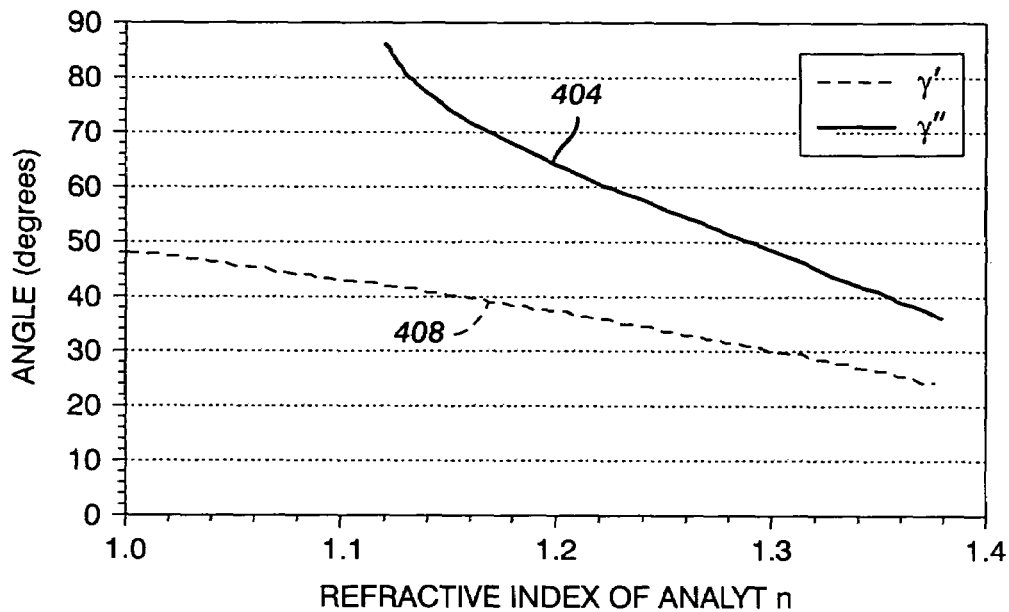
FIG. 4 is a chart that plots an angle of incidence into the waveguide structure of FIG. 2 as a function of the index of refraction of the sample.

FIG. 4 plots the data shown in FIG. 3. As shown in curve 404 of FIG. 4, the angle of incidence increases with decreases in the sample refractive index. At sample refractive indices less than 1.15 (n<1.15), it is very difficult to couple light into the waveguide facette and generate desired anti-resonant modes. Even for n>1.15, the optimum angles for generating anti-resonant modes are still larger than what may be suitable for coupling large amounts of light into the sample. Large angles create difficulties because these angles force the use of smaller diameter beams to hit the facette at the large angles. Furthermore, the use of large angles substantially increases reflection losses.

Figure 5:
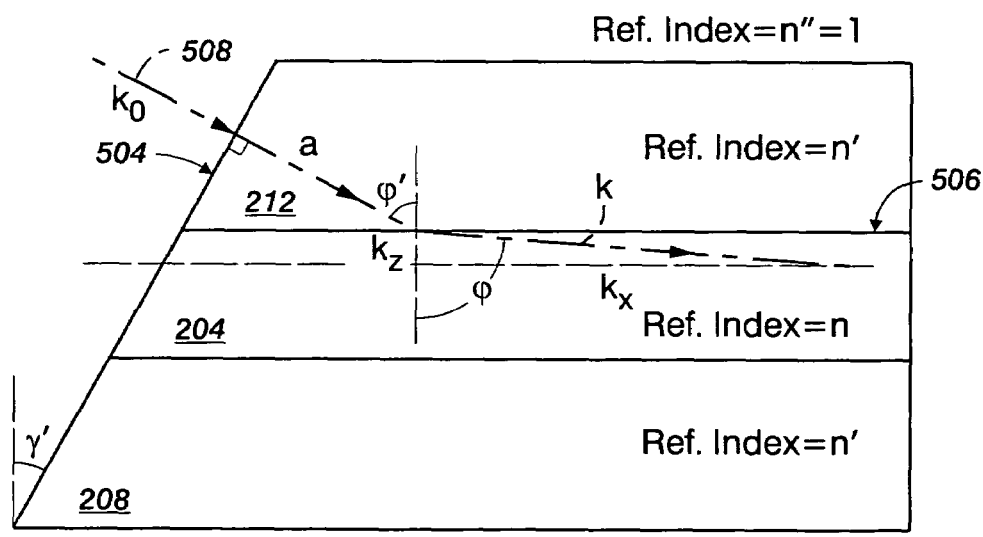
FIG. 5 shows a side sectional view of a waveguide with a biological sample as a core and with a tilted entrance facette.

FIG. 5 shows an alternate structure of FIG. 2 that minimizes losses caused by large incident angles. In FIG. 5, the entrance facette 504 is tilted. Reflections at the facette are minimized when incidence beam 508 perpendicularly enters entrance facette 504. By adjusting the tilt angle γ' such that a beam perpendicularly enters facette 504 and still strikes the cladding and sample interface 506 at an angle φ' suitable to create an anti-resonant mode, reflections from the facette can be minimized while still generating the desired anti-resonant modes.

FIG. 3 shows tilt angles γ' for the structure of FIG. 5 that corresponds to various analyte refractive indexes. By tilting the entrance facette 504, generation of anti-resonant optical waves in analytes with refractive indices that range down to n=1 becomes possible. Generating anti-resonant optical waves in low index samples enables the use of gas and aerosol samples. Note that in this case the refractive index of the surrounding medium n" might be chosen smaller than the refractive index of the medium n in order to also allow higher anti-resonant waveguide modes to be guided with reasonable leakage loss.

Although two geometries and end facette designs have been provided in FIG. 2 and FIG. 5, these geometries are provided as examples only. It is possible to use other geometries and end facette designs to couple light into an anti-resonant propagating wave. Examples of other geometries include curved end facettes and cylindrical sample shapes rather than the angular end facettes and slab structures described. How to couple light into these other geometries in order to generate an anti-resonant wave in the sample can be determined by solving, either mathematically or numerically the general Helmholtz equation for these geometries. Such calculations are known to those of skill in the art. Thus the scope of the invention should not be limited to the particular example analyzed herein.

Figure 7:
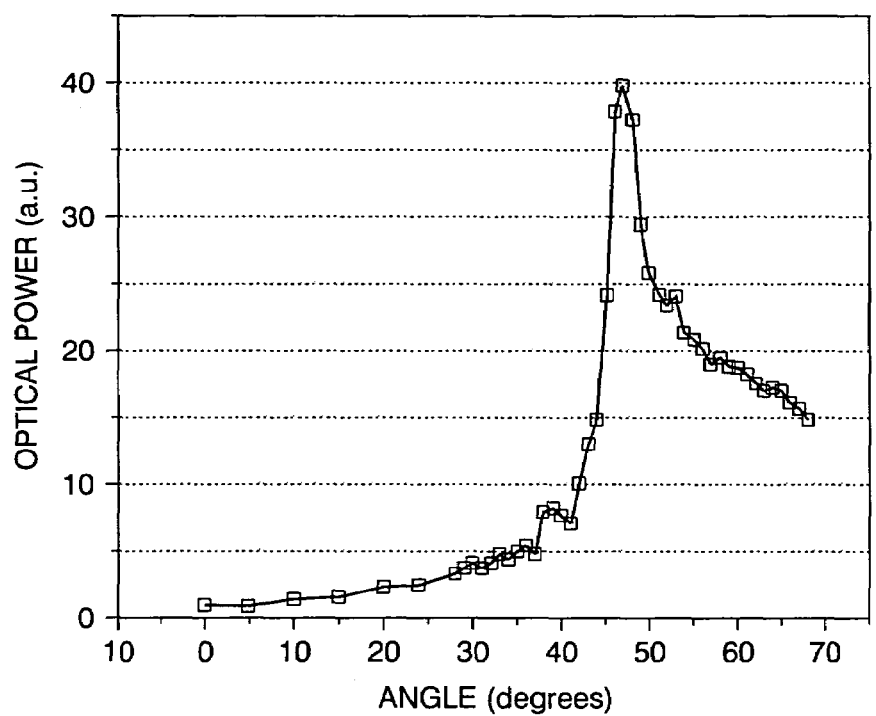
FIG. 7 shows the fluorescence intensity as a function of the coupling angle of the excitation light.

FIG. 7 is a plot of the actual florescent intensity output from a sample as a function of a coupling angle of excitation light into the sample. As will be described, the experimentally generated results of FIG. 7 match closely the theoretical expected coupling efficiencies at various angles of light input.

In order to generate the graph of FIG. 7, excitation light from a single blue high powered LED was coupled at various angles into a side of a liquid film placed between two glass slides. The excitation light excited a fluorescein dye in the liquid film and resulted in fluorescence throughout the entire film area (an area of 25×75 mm$^2$). The resulting fluorescence was then measured.

In the measurements, the measured fluorescence intensity per unit area was similar to that which has been obtained by perpendicularly (from the top) focusing the total excitation power from the LED onto a small spot (e.g. 3×3 mm$^2$) in the sample. The improved fluoresce results from a more efficient use of the excitation light by coupling the light into an ARGOW, in particular, guiding the light between the glass slides. This compares favorably to regular fluorescence detection when the excitation light is input perpendicular to the sample plane and results in transmission of most of the light. Using anti-resonant waveguide excitation the sample itself guides the excitation light between the glass slides providing a long interaction length between light and fluorescent molecules. FIG. 7 plots the fluorescence intensity as a function of the coupling angle of the excitation light. The experimental value for optimum coupling efficiency is in excellent agreement with the theoretically predicted value.

FIG. 6 shows the refractive index profile and the normalized mode intensity of 3 anti-resonant modes of a glass/water/glass anti-resonant waveguide. The anti-resonant modes are calculated assuming 480 nm wavelength light and a 15 μm thick liquid film between two glass slides. The predicted confinement factors for these modes within the liquid film are quite large. For the first three modes confinement factors of $\Gamma=0.9$, 0.8 and 0.55 respectively were obtained.

Each mode can be specifically excited by adjusting the incidence angle $\phi$ (the angle 120 of FIG. 1). The anti-resonant modes with the highest confinement factors can be excited at a glancing angle $\phi=46.5°$. Glass cladding thickness variations will usually not affect this angle because glass thicknesses are large compared with the wavelength of the propagating light (even if infrared light is used). Changes in liquid film thickness can change the optimum incidence angle; however, calculations show that the effect is very small. Reducing the thickness of the liquid film from 15 μm to 5 μm changes the optimum glancing angle $\phi$ from about 46.5° to only about 46.6°. Because within a window of about 0.5 degree, there is available a number of modes with reasonably high confinement factors, the slight change in optimum glancing angle does not present difficulties for the actual system.

Changes in light wavelength also produces slight changes in optimum incidence angle. For example, substituting infrared light (~1500 nm) for blue light (~480 nm) only changes the optimum incidence angle by about 1.8°. The difference in the dispersion of glass and water has a larger influence compared to the different confinement conditions for the different wavelengths which have only small impact on incidence angle.

Figure 8:
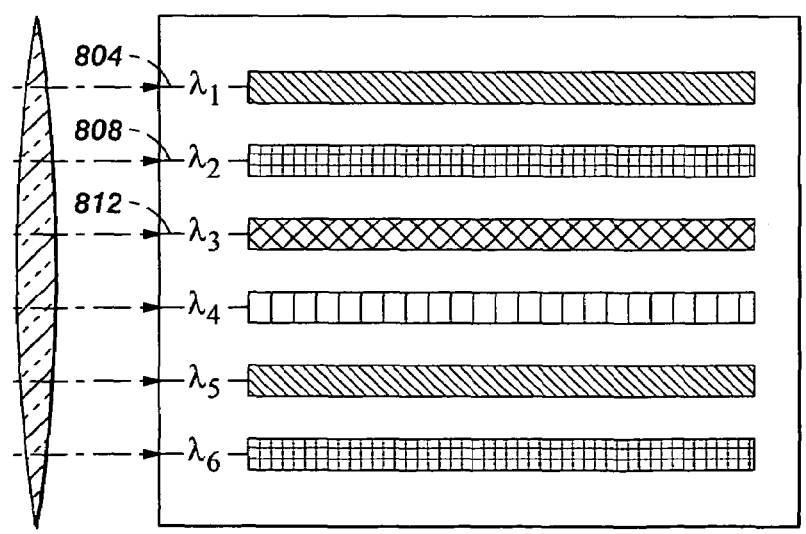
FIG. 8 shows a top view of a system to process in parallel different tests on a sample to determine the presence of a target analyte.

The ability of the overall system to accommodate changes in light frequency and sample thickness makes it ideal for use in parallel analytic techniques. These are particularly useful in sophisticated systems where several different tests are to be conducted in parallel to determine the composition or presence of various target analytes. FIG. 8 shows a top view of a sample 800 receiving several frequencies of light 804, 808, 812 at once. Each frequency of light could correspond to a different test to be performed on the sample.

Figure 9:
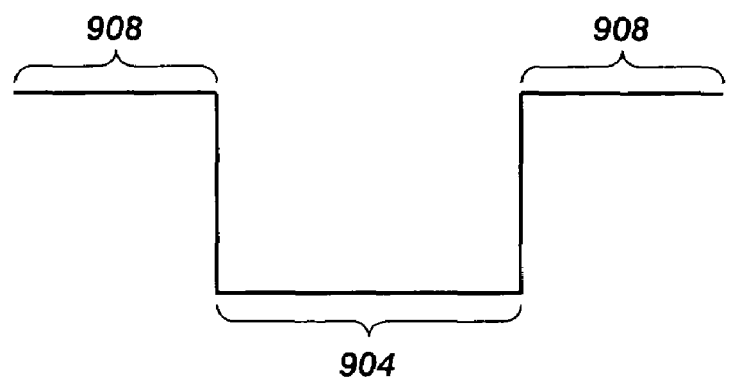
FIGS. 9-14 show sample index profiles of a sample and cladding immediately adjacent the sample.

In the preceding discussion, analysis has been done on step index profiles such as that shown in FIG. 9. However, the generation of ARGOWs should not be limited to such index profiles. FIGS. 9-14 show other index profiles where an index of refraction through the cladding and sample is plotted along a vertical axis and the distance along a cross section of the cladding and sample is plotted along a horizontal axis. As was previously explained, the thickness of the cladding layers is not critical and can be chosen within a wide range. Depending on the application and method of forming the cladding, the thickness of the cladding in one example embodiment is approximately 1 mm (e.g. if glass slides are used). In other cases the cladding may be chosen very thin, not more than three or four wavelengths of the propagating light.

Figure 10:
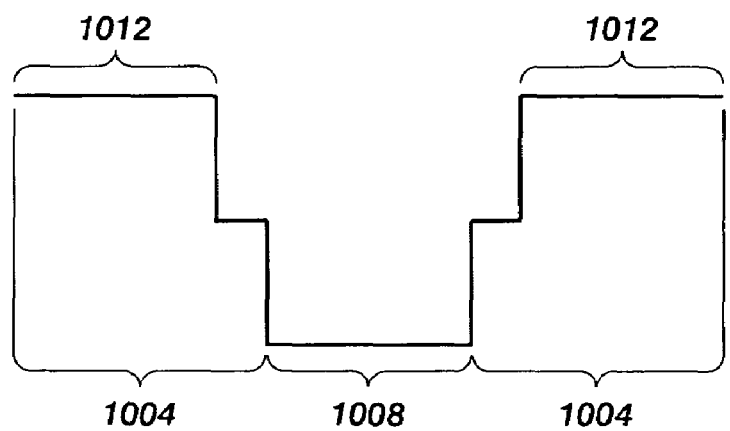

FIG. 10 shows a two step function where cladding region 1004 surrounding sample region 1008. Cladding region 1004 includes two steps in the index of refraction. Systems where a coating is used to prevent sticking of the analyte or other parts of the sample to the sample chamber or medium walls might exhibit such an index of refraction profile. For example, a teflon coating used in cladding region 1004 to coat a glass medium might be a typical example. Teflon has an index of refraction of 1.38 between the glass medium 1012 index of refraction (about 1.44) and a water based sample index of refraction.

Figure 11:
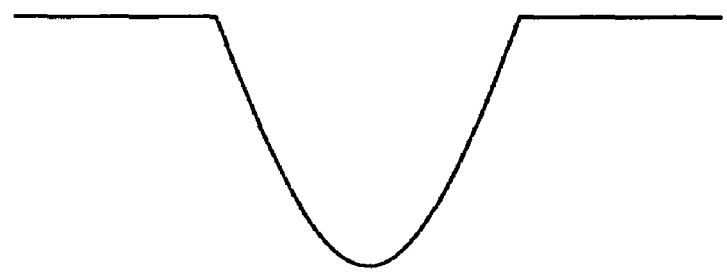
Figure 12:
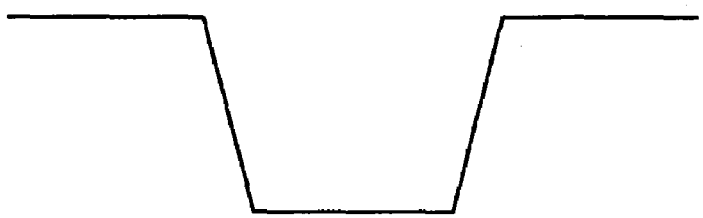
Figure 13:
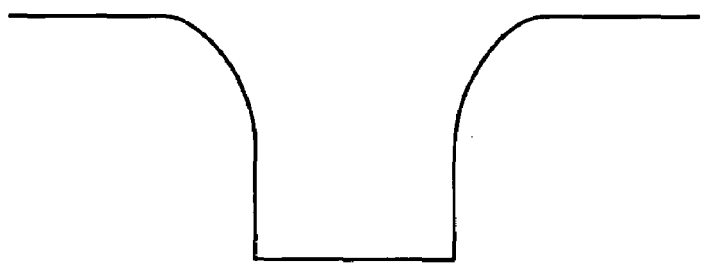
Figure 14:
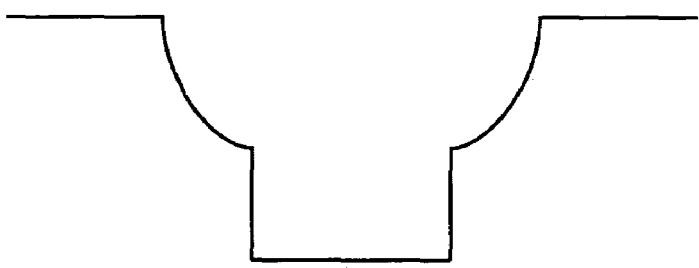

FIG. 11 shows that the sample itself does not have to have a constant index of refraction. FIG. 11 shows a parabolic index of refraction profile that may be exhibited by a fluid sample flowing at different speeds through a medium (e.g. causing phase separation of a mixture). Other monotonically increasing indexes of refraction (monotonically increasing from the edge of the sample through the cladding layer) are shown in FIGS. 12-14. Monotonically increasing indexes of refraction through the cladding region minimizes reflections that may occur from the cladding layers.

Returning to FIG. 1, once an ARGOW propagating wave is generated in the sample, the resulting interaction of the light with the sample contents may be analyzed for information. In one embodiment, a detector 140 of FIG. 1 detects the light that propagates through the sample. In an alternate embodiment, a detector 144 of FIG. 1 detects light that is scattered or refracted by the sample. Depending on the target (e.g. bioagent) to be detected and the particular detection technique to be used, detectors 140, 144 may include wavelength sensitive elements such as gratings, prisms, Bragg reflectors or resonators.

Wavelength sensitive elements enable identification of signatures and specific biological or chemical agents. Detectors 140, 144 may also integrate the wavelength sensitive elements with conventional optics or micro-optics components including mirrors and lenses. In some embodiments, the detectors may include a means for converting the optical signal to an electrical signal. Such conversions may be achieved using a charge coupled device, a photosensor, or any of a variety of conversion devices. Once converted to an electrical signal, detector 140, 144 output can be analyzed using electric processors, such as microprocessors (not shown).

Detector 140 of FIG. 1 detects light transmitted by sample 116. In one embodiment, the light transmitted by sample 116 is analyzed by processors coupled to the detector to determine the presence or absence of chemical, environmental or biological molecules in sample 116. The output of detector 140 may also be used to analyze the characteristics of molecules in sample 116. An example of using detectors to detect light transmitted by a sample and a processor to analyze the detector output is provided in U.S. Pat. No. 6,603,548 entitled "Biosensor" by Church et al. which is hereby incorporated by reference in its entirety.

In an alternate embodiment, instead of detecting light that is transmitted, a second detection system such as detector array 144 may detect light that is scattered or otherwise output by sample 116. Scattered light may be caused by reflection or refraction of light by molecules in sample 116. Example scattering techniques include elastic and inelastic light scattering spectroscopy as described in Introduction to Biophotonics, by Paras N. Prasad ISBN 0471-28770-9, Wiley-Interscience 2003) which is hereby incorporated by reference in its entirety.

In still another embodiment, light output from sample 116 may be caused by fluorescence that results from binding of chemical elements in the sample to biological materials. The binding results in fluorescence when an excitation source, such as the anti-resonant light propagating in the sample is present. U.S. Pat. No. 6,577,780 by Lockhart entitled Cell Designs for Optical Sensors describes using antigens that attach to antibodies resulting in a structure that fluoresces in the presence of an evanescent field. U.S. Pat. No. 6,577,780 by Lockhart is hereby incorporated by reference in its entirety. By using anti-resonant waves propagating through the sample instead of evanescent fields, the sensitivity of the system can be improved.

Besides the examples given, many other optical detection and sensing techniques may be used with sensors 140 and 144. Those techniques include, but are not limited to single or multicolor light-induced intrinsic fluorescence or fluorescence from tagged molecules and applications derived from the manipulation of the fluorescent lights such as fluorescence lifetime imaging microscopy (FLIM), fluorescence resonance energy transfer (FRET), fluorescence correlation spectroscopy (FCS), etc., light scattering or vibrational spectroscopy (Raman, IR) or spectroscopic applications utilizing optical activity of chiral media such as circular dichroism (CD), among others. A more detailed description of various detection techniques utilizing photon interactions is provided in Chapter 4 of "*Introduction to Biophotonics*" by Paras N. Prasad, ISBN 0471-28770-9, Wiley-Interscience 2003), which is hereby incorporated by reference.

Figure 15:
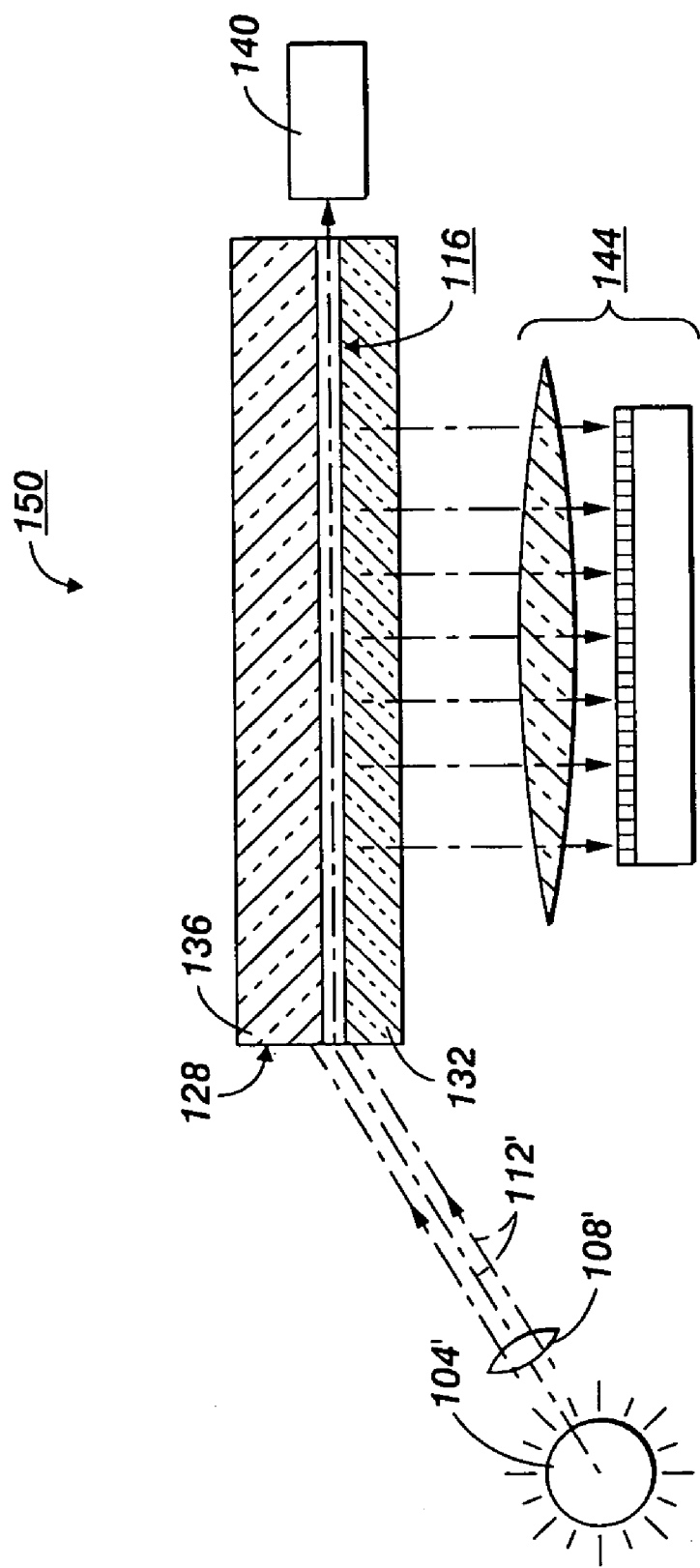
FIG. 15 shows a side sectional overview of a second embodiment of an analysis system similar to FIG. 1.

With continuing attention to FIG. 1, optical sensing system 100 is illustrated with light source 104 and/or lens system 108 directing light beam 112 into sample 116 from a position above covering layer 136. It is to be appreciated and as more particularly illustrated in FIG. 15 alternatives to this light input arrangement are possible. For example, in optical sensing system 150, light source 104' and/or optics 108' are arranged such that light beam 112' is directed to sample 116 from a position below substrate 132. The appropriate incident angle may be determined in a manner as previously discussed in connection with the light source arrangement of FIG. 1.

Figure 16:
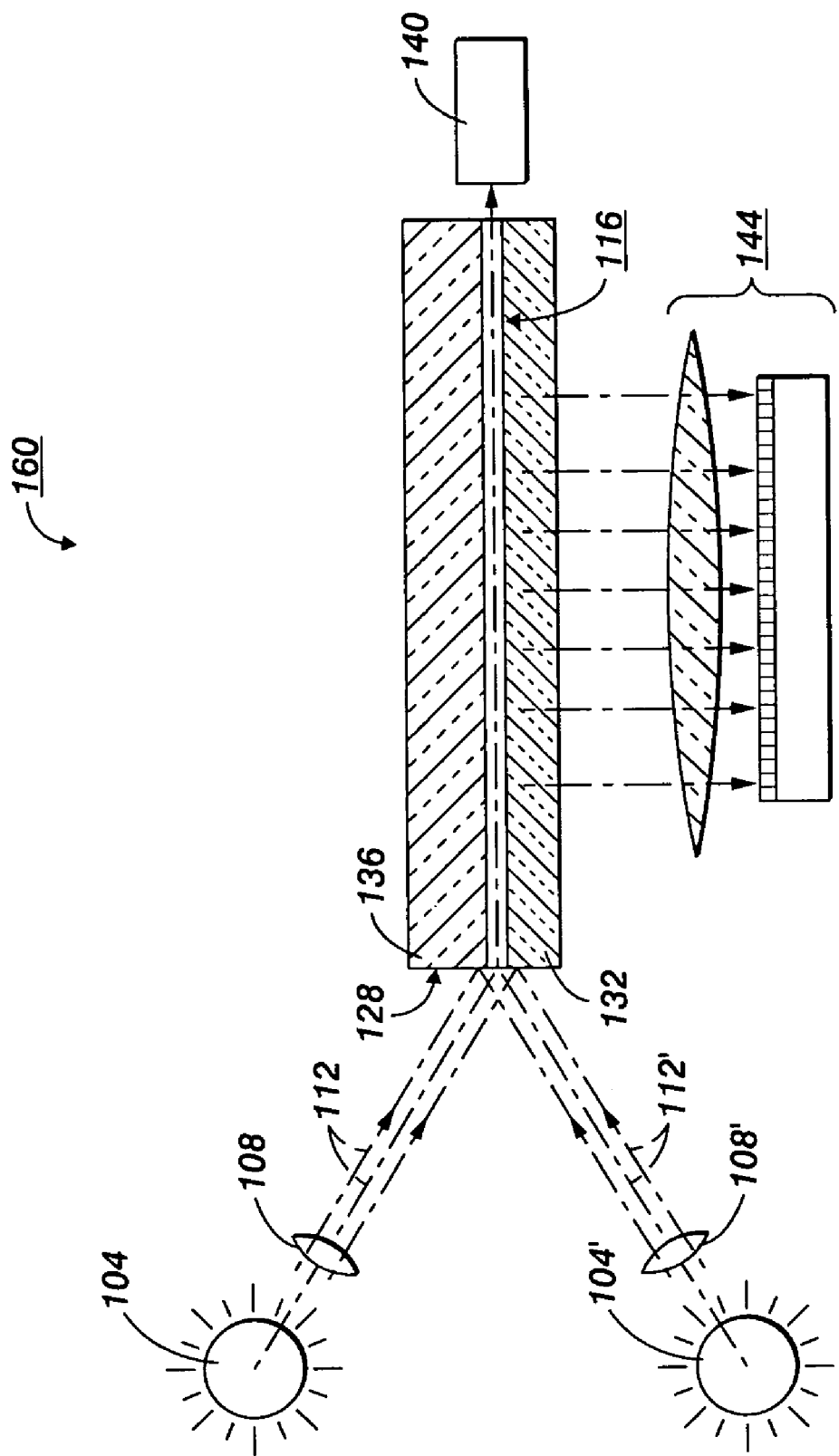
FIG. 16 shows a side sectional overview of a third embodiment of an analysis system similar to FIG. 1.

As illustrated in FIG. 16, in addition to use of light source 104 and/or lens system 108, light source 104' and/or a lens system 108' are provided to deliver light beam 112' in optical system 160. In this system, light sources 104 and 104' can be selected to provide light at distinctly different wavelengths in order to excite dye tags having distinct operational characteristics. Alternatively, light sources 104 and 104' may operate in a similar wavelength range, when used in a system which controls the operation of light sources 104, 104' to avoid overlapping operational time periods, thereby minimizing undesirable light interactions. For example, high speed on/off switching control of light sources 104, 104' are one implementation which would avoid undesirable overlapping. Again, the appropriate incident angles for the above embodiments may be obtained through use of the previously described procedures. Additionally, a light beam spread over multiple frequencies may be coupled to the waveguide (i.e., sample 116, substrate 132 and covering plate 136) by using a light source having a less coherent beam, which thereby can excite dyes having different excitation frequencies.

Figure 17:
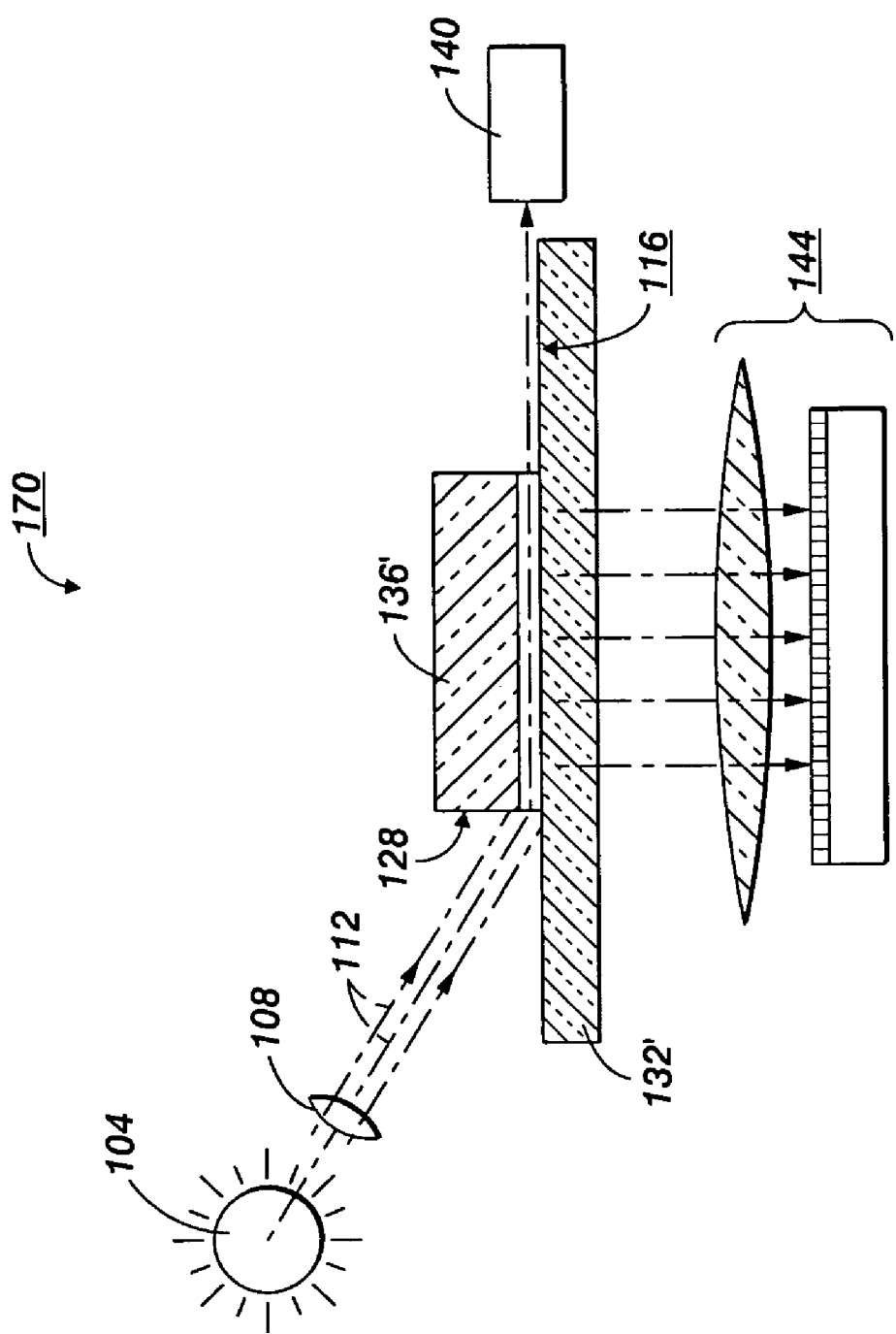
FIG. 17 shows an expanded side sectional view of a third embodiment of a waveguide with a biological sample as a core, and with a non-sysmetric substrate and covering layer.

Turning attention to FIG. 17, in the discussion related to FIGS. 2 and 5, it has been shown that different geometries may be used for the end facet designs. Particularly, in FIG. 2, the end facets are substantially flat matching end pieces perpendicular to the horizontal, whereas FIG. 5 shows a tilted entrance facet configuration. In addition to these configurations, it is to also be understood the substrates and covering layers may be of different sizes from each other. For example, substrate 132' is substantially longer than covering layer 136' in optical system 170. In this embodiment, light source 104 is positioned to have light beam 112 enter sample 116 at the appropriate incidence angle through the end facet of covering layer 136'. Thus, substrates 132, 132' and covering layers 136, 136' do not need to be of the same length or thickness, or symmetric to each other.

Figure 18:
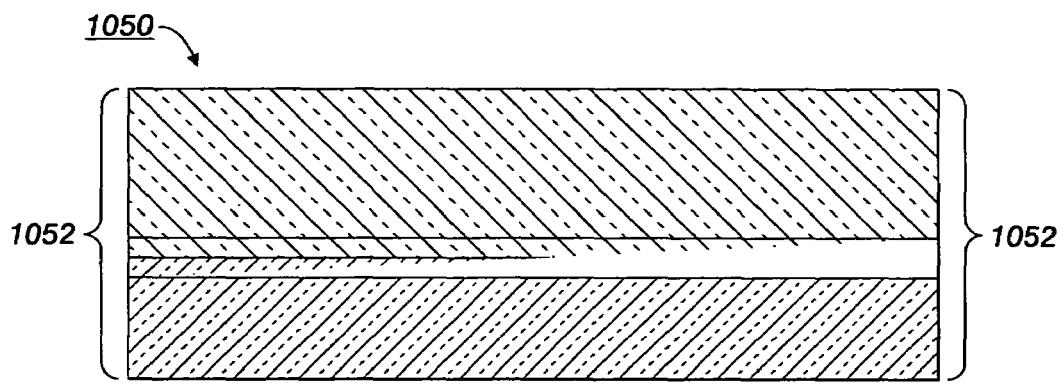
FIGS. 18-21 depict the use of an outer metalized light containment component in combination with the anti-resonant waveguide structure.
Figure 19:
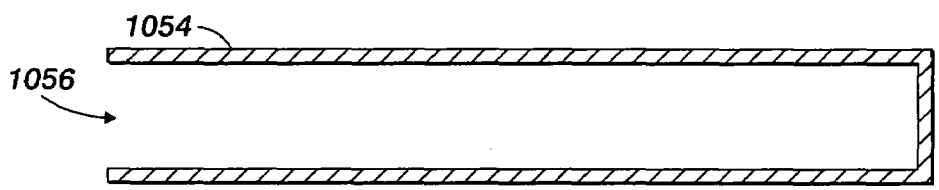
Figure 20:
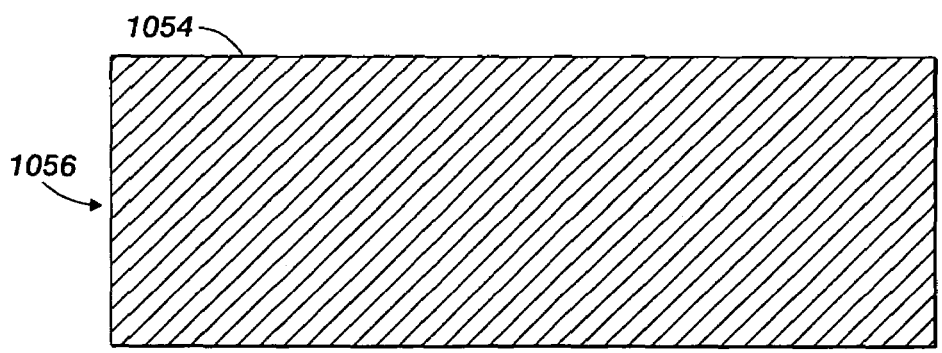
Figure 21:
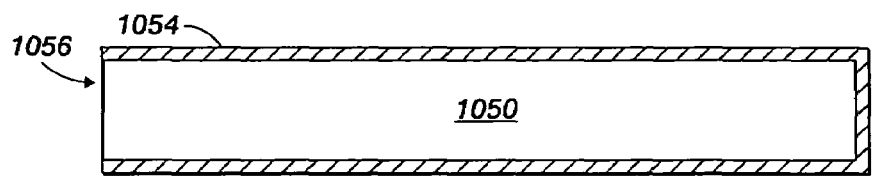

As described in the foregoing, the use of the anti-resonant waveguide permits for the excitation light to be guided between the glass slides, and therefore provide increased interaction between the excitation light and the fluorescent molecules. Therefore, the anti-resonant waveguide concept more efficiently uses the light from the light source. However, an area where light is most likely to escape from the waveguide is at the surrounding end facets 1052, which as shown in FIG. 18, extend around the entirety of waveguide 1050. As there is no containment of the light at the end facets 1052 of waveguide 1050, this is a location where portions of light beam 112, 112' (FIGS. 15-17) may be lost. To provide increased containment of light beam 112 (112') within the anti-resonant waveguide, light retention component 1054 (shown in top view in FIG. 19 and side view in FIG. 20) is provided. In this embodiment, light retention component 1054, is made of a reflective material, such as a metal mirror material or dielectric Bragg mirror, configured as a single unitary three-sided component sized to closely engage interface end facets 1052 of waveguide 1050. As depicted in the top view of FIG. 21, when light retention component 1054 is positioned around end facts 1052, light 112 (112') inserted via open end 1056 is contained within the waveguide, providing increased excitation efficiency.

Figure 22:
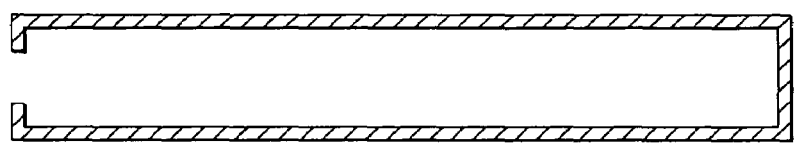
FIG. 22 shows an optional arrangement for the outer metalized light containment component of FIG. 19.

Turning to FIG. 22, depicted is an alternative light retention component 1054'. In this design, reflective material ends. Particularly, the ends should extend only to a position which permits light to be coupled into the anti-resonant waveguide may be included to partially extend over open end 1056. The amount of open end 1056 covered by reflective material ends 1057 will depend on the spot size of the incoming light.

Figure 23:
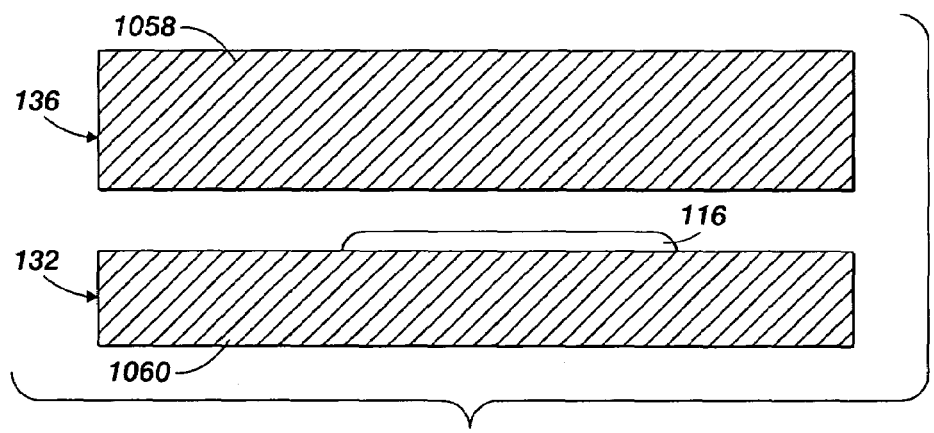
FIGS. 23-24 show top and side views of a second embodiment of a light containment component.
Figure 24:
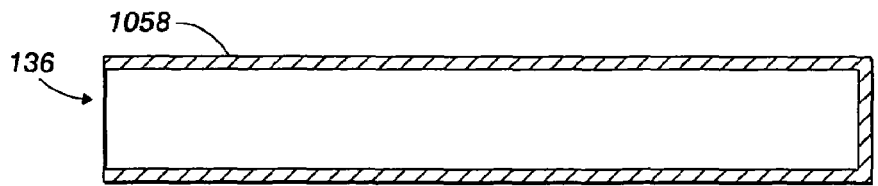

In an alternative embodiment, FIGS. 23-24 illustrate, respectively, side and top views of a light retention configuration in which substrate 132 and covering layer 136 are provided with separate reflective mirror members 1058 and 1060, respectively, prior to positioning substrate 132 and covering layer 136 together with sample 116. It is to be appreciated sample 116 may be specifically bound to either of the substrate 132 or covering layer 136, or may be moving around within the medium between the substrate and covering layer. Retention members 1058, 1060 may be configured to be permanently or removably attached to substrate 132 and coving layer 136.

Figure 25:
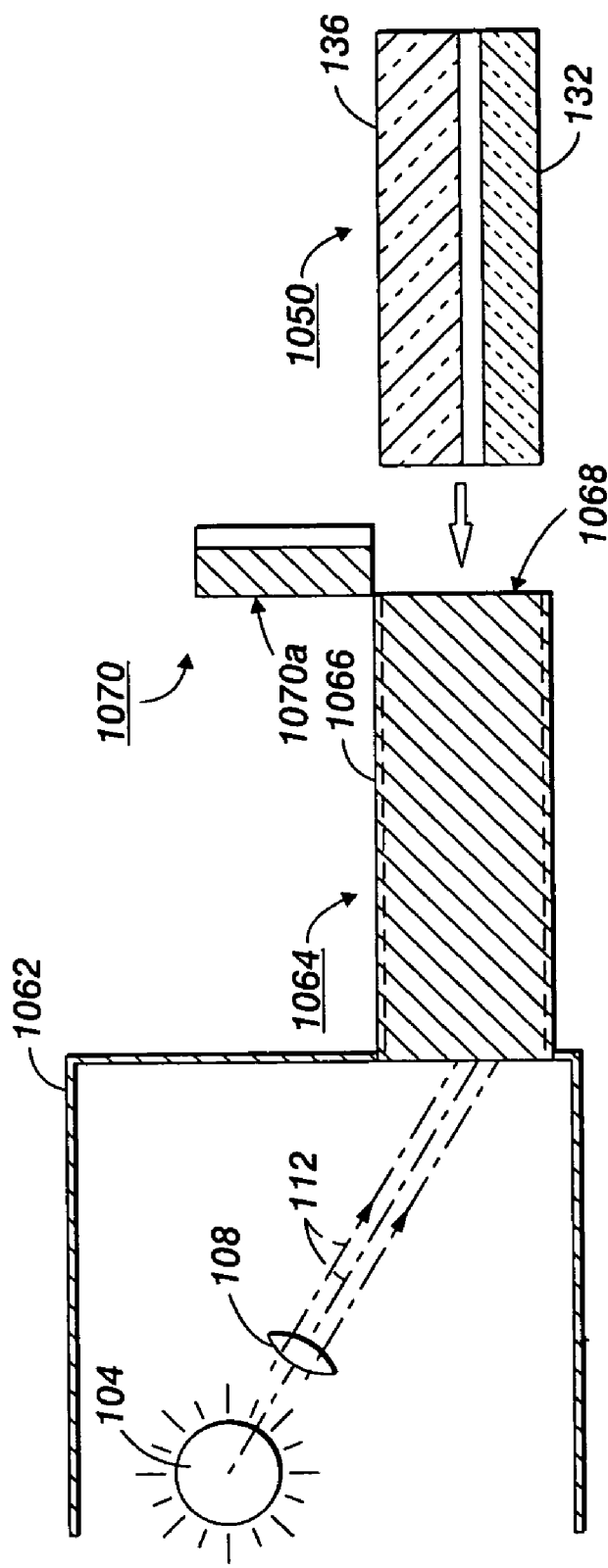
FIGS. 25-26 show side views of an input portion of a detection device incorporating a light containment configuration therein for use in conjunction with an anti-resonant waveguide.
Figure 26:
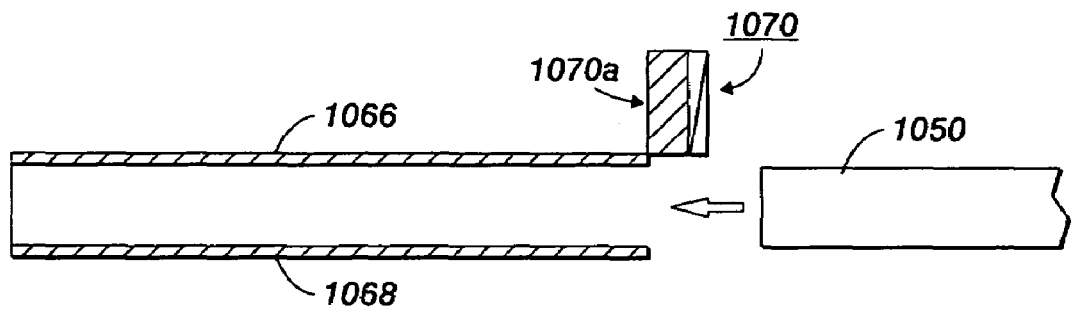
Figure 27:
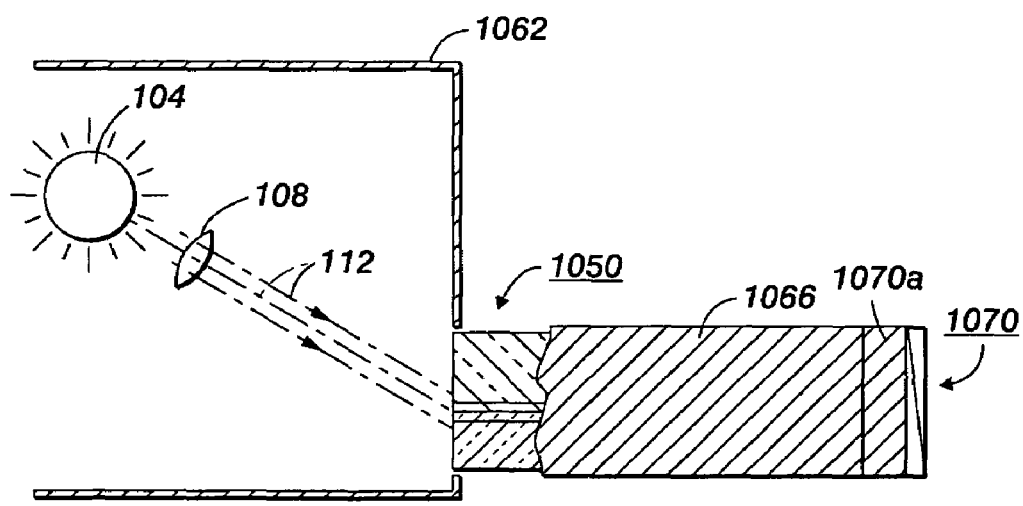
FIG. 27 shows a portional top view of FIGS. 25 and 26.

In still a further embodiment, FIGS. 25-27 depict a sample detection device 1062 constructed with an internal reflective light retention mirror configuration, such that once waveguide 1050 is positioned within sample detection device 1062, additional containment of the light is achieved.

For example, FIG. 25 is a partial side view of sample detection device 1062, which includes input area 1064, and light source 104 and lens 108. The input area 1064 is configured and dimensioned to receive anti-resonant waveguide 1050. As more clearly shown in the top view of FIG. 26 input section 1064 includes first mirror surface 1066, second mirror surface 1068 and door 1070, with an inner mirror surface 1070a. As shown in FIG. 27, once waveguide 1050 is moved into input area 1064, door 1074 is closed. By proper dimensioning, waveguide 1050 is then in close engagement with reflective mirror portions 1066, 1068 and 1070a. By this design light beam 112, coupled to waveguide 105, is maintained and concentrated within the waveguide in a manner similar to that discussed in connection with FIGS. 18-24.

The concepts discussed in connection with FIGS. 18-27 are equally applicable to the waveguide arrangements of FIGS. 5 and 17, as well as other differently sized or dimensioned waveguides, by adjusting configurations of the light retention components to match the specific waveguide configuration.

It is also to be understood, excitation light beams (e.g., 112, 112') have been shown to be either directly provided or provided through optics to the anti-resonant waveguide. Therefore, the light beams can be coupled into the anti-resonant modes using free-space optics or by conventional waveguides such as glass fiber, glass bundles or planar optical waveguides as examples. The previous drawings are intended to represent such known coupling techniques. Further, while light beams (112, 112') are depicted in the foregoing discussion as being entered at an end of the waveguide, in still a further embodiment, it is considered that the light beams (112, 112') are positioned to enter the waveguide through a side of the waveguide. In this embodiment, multiple or less coherent light sources may be used to provide a wider width of coverage. Further, containment components in this embodiment would be designed to permit the light beam (112, 112') to enter through the side facet.

A particular aspect of the present application is that through increasing the maintenance of light within the anti-resonant waveguide, and thereby improving excitation light efficiency, it is possible to improve the overall fluorescence efficiency. A beneficial feature of the improved efficiency of fluorescence is the ability to implement fluorescent based readers in a more compact, low cost configuration. More particularly, and as previously mentioned, in existing systems the common light source used in, for example, a conventional white light system (i.e., one which employs white light sources) may be various ones of the xenon, halogen or deuterium lamps having characteristics such as:

Xenon DC lamp (75 W): ~5 mW $m^{-2}$ $nm^{-1}$ at a distance of 0.5 m fairly evenly distributed over almost the entire wavelength range (300-1000 nm), drops off below 300 nm.

Xenon flash lamp (60 Hz, 60 W average power): >2 mW $m^{-2}$ nm-1 at a distance of 0.5 m over almost the entire wavelength range (200-1000 nm), stronger in the deep UV.

Hg (optics) lamp (500 W, DC): ~0.2 mW cm-2 nm-1 at a distance of 0.5 m for main peaks at 365 nm, 404 nm, 435 nm and 546 nm; ~0.1 mW cm-2 nm-1 at a distance of 0.5 m for smaller peaks at 313 nm and 576 nm (without collimating optics and filters); all other wavelength much lower.

Hg lamp (500 W, DC): ~1 W for main peaks at 365 nm, 404 nm, 435 nm and 546 nm; ~0.2 W for smaller peaks at 334 nm (includes collimating optics and filters, beam size 50×50 mm2).

Deuterium lamp (30 W, DC): 0.1 to 1 mW m-2 nm-1 at a distance of 0.5 m between 400 nm and 200 nm (linearly increasing with shorter wavelength).

Quartz Tungsten Halogen lamp (QTH lamp) (100 W, DC): Continuous spectrum peaking at ~900 nm; 25 mW m-2 nm-1 at a distance of 0.5 m at 500 nm, 10 mW m-2 nm-1 at 400 nm, 5 mW m-2 nm-1 at 350 nm, 2 mW m-2 nm-1 at 300 nm.

Table 1 summarizes light power of the above lamps, where the light power is focused onto a 15×20 $mm^2$ area for the different light sources (estimated for a spectral width of 10 nm).

TABLE 1

| Lamp | Xenon DC | Xenon flash | Hg (lamp) | Hg (optics) | Deuterium lamp | QTH lamp |
|---|---|---|---|---|---|---|
| Power | 10 mW | 4 mW | 2-4 W | 0.2-1 W | 0.2-1 mW | 4-50 mW |

In existing systems, these high-powered, physically large lamps are necessary in order to generate sufficient emissions within absorption range of existing fluorescent dyes, such as those shown in Table 2.

TABLE 2

| Dye | Absorption | Emission |
|---|---|---|
| Alexa Flour 350 | 346 nm | 442 nm |
| Alexa Flour 546 | 556 nm | 572 nm |
| Alexa Flour 594 | 590 nm | 617 nm |
| Alexa Flour 660 | 668 nm | 698 nm |
| BFP | 381 nm | 445 nm |
| Bodipy FL ATP | 505 nm | 515 nm |
| Bodipy TMR | 542 nm | 574 nm |
| Cy2 | 489 nm | 506 nm |
| Cy3 | 550 nm | 565 nm |
| Cy5 | 650 nm | 690 nm |
| DAPI | 359 nm | 461 nm |
| FITC | 494 nm | 518 nm |
| Lucifer Yellow | 435 nm | 532 nm |
| ROX | 576 nm | 601 nm |
| Texas Red | 595 nm | 620 nm |

By use of the anti-resonant waveguide concepts of the present application, it is possible to use less powerful, much smaller and less expensive light sources such as LEDs, LDs and SLEDs. Benefits and operational characteristics of these devices are discussed below. It is of course to be understood that a conventional light source can be used in combination with the anti-resonant waveguide concepts described herein.

High power UV, visible, and IR LEDs are commercially available. For example, the Luxeon V Star power LEDs are offered in the wavelength range between 430 nm to 550 nm, covering the blue and green portions of the light spectrum. The spectral width (FWHM) ranges between 20 nm (@ 430 nm) and 35 nm (@ 550 nm). These LEDs are specified to run at 700 mA dc with operating voltages below 7V. DC output power under these operating conditions are between 500 mW for royal blue (440 nm-460 nm) and about 100 mW for green (520 nm-550 nm). High efficiency yellow, orange and red LEDs in the wavelength range between 590 nm and 650 nm are also commercially available. External quantum efficiencies in that wavelength region range between 20% (590 nm) to 55% (@ 650 nm). Incorporated in a high power heat sink package, these efficiencies correspond to output powers between 100 mW (@590 nm) and 260 mW (@650 nm) for a DC drive current of 250 mA. Higher output powers are possible with higher drive currents and improved heat-sinking.

LEDs from other sources at shorter wavelengths have also been demonstrated. External quantum efficiencies of 30-40% have been reported for InGaN LEDs emitting between 380 nm and 410 nm. Packing those LEDs into high power LED packages, result in output powers in the range between 600 mW and 800 mW (at drive currents of 700 mA). Progress has been reported on a 365 nm UV LEDs with output powers of 100 mW. Researchers at Palo Alto Research Center (PARC) of Palo Alto, Calif. and LumiLeds Lighting of The Netherlands, have reported a 30 mW UV LED emitting around 370 nm. Table 3 summarizes output power levels for single chip LEDs at different emission wavelengths for the above discussed devices.

TABLE 3

| Wavelength | 370 nm | 400 nm | 450 nm | 530 nm | 590 nm | 650 nm |
|---|---|---|---|---|---|---|
| Power | 30 mW | 700 mW | 500 mW | 100 mW | >100 mW | >260 mW |

Another light source which may be used in accordance with the present concepts are superluminescent light emitting diodes (SLEDs) which have been shown to be optimum light sources in optical coherence tomographs (OCTs), fiber sensor and optical coherence domain reflectometer (OCDR) applications because of their wide bandwidth and high output power. Currently, SLED devices based on GaAs/or InP material system are commercially available at 820 nm, 1300 nm and 1550 nm windows from different vendors (e.g. InPhenix Corporation of Livermore, Calif. and Exalos AG of Zurich, Switzerland).

SLED is an edge-emitting semiconductor light source. The unique property of an SLED is its high output power and high power density, similar to an injection laser diode (LD), but with a broad emission spectrum and low coherence, similar to a light emitting diode (LED). SLEDs are based on stimulated emission and similar in geometry to lasers but have no built-in optical feedback mechanism required by LDs for stimulated emission to achieve lasing. A main difference for SLED operations compared to LEDs is SLEDs have a higher gain and higher current density. A main difference for SLED operations compared to LDs is SLEDs have a stronger non-uniformity of photons and carrier density distribution inside the active region. SLEDs have structural features that suppress the lasing action by reducing the reflectivity of the facets. SLEDs may be considered essentially highly optimized LEDs. While SLEDs operate like LEDs at low current levels, their output power increases superlinearly at high currents. There are six key parameters used to characterize SLEDs: (i) Output Power, (ii) Optical Gain, (iii) ASE Spectrum Bandwidth or 3 dB Bandwidth, (iv) Spectrum Modulation or Ripple, (v) Coherence Length, (vi) Coherence Function. Every SLED has two counter-propagating beams of amplified spontaneous emission traveling along the active region. A perfect SLED would be an optimized traveling wave laser diode amplifier with zero reflection from the active channel ends. However, a perfect SLED is virtually impossible to realize due to the physical limitations of some of the manufacturing processes such as antireflection coatings (AR).

Thus, in place of the light sources used in existing systems, through implementation of the present concepts it is possible now to manufacture fluorescence devices employing much smaller, compact and efficient lighting sources (e.g., LEDs, LDs and/or SLEDs), than now possible in existing fluorescence detection devices. Thus, systems employing LEDs, LDs and SLEDs offer a number of advantages compared to conventional light sources including:

Longer lifetimes: Typically >100000 hours for LEDs vs. few hundred or a couple of thousand hours for conventional light sources Lower cost: $5-20 for an LED vs. hundreds or thousands of dollars for high power Hg lamps setup (not including replacement costs)

No warm-up time

DC operation and pulsed operation possible with same setup (LED pulse length can be electronically controlled).

Much higher efficiencies (=low power consumption)

No special power supply required (low voltage, low current)

Very stable light output (low noise)

Spectrally narrow (makes filter selection easier).

Non-toxic materials (no mercury)

More directional emission (makes optics simpler and cheaper)

Figure 28:
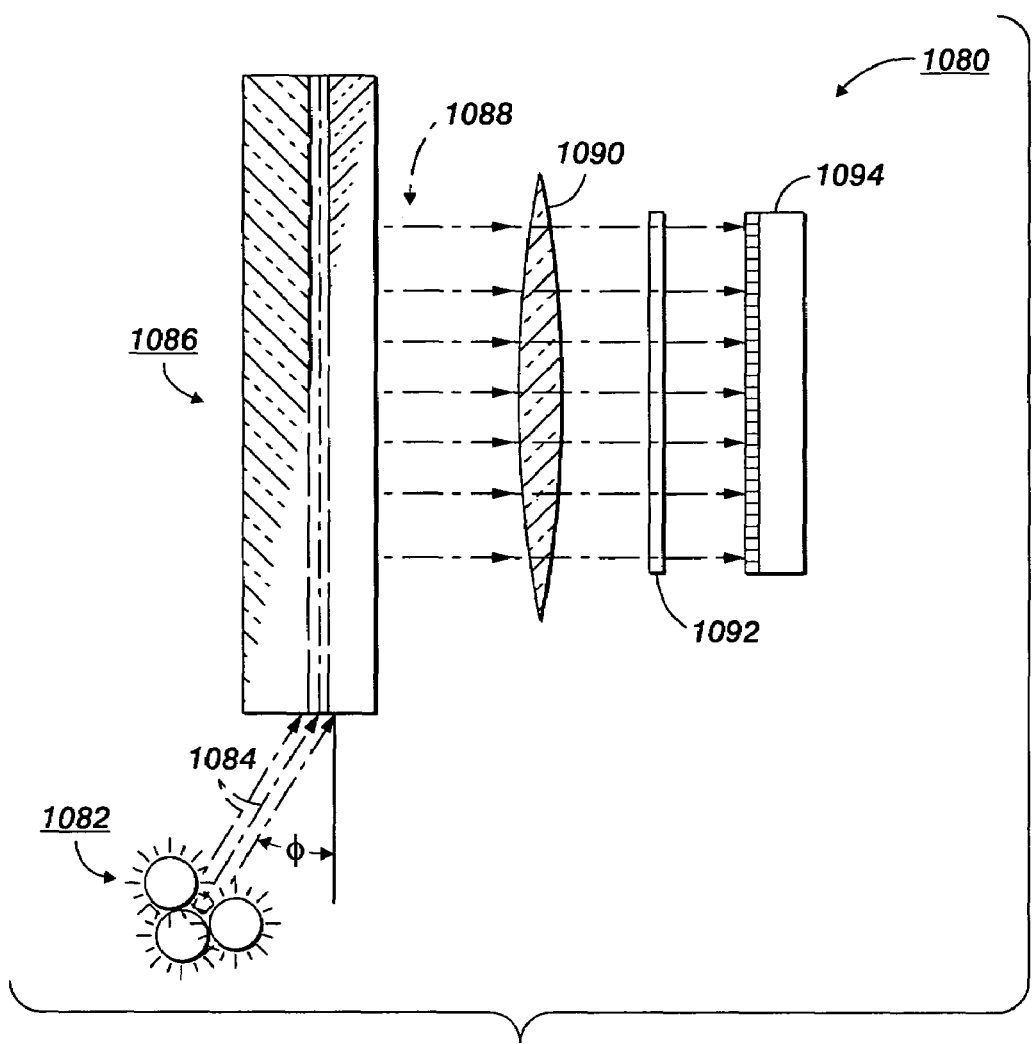
FIG. 28 shows a detector where the light source uses LEDs, LDs and/or SLEDs.

In consideration of the above, shown in FIG. 28 is a compact, low cost sample reader 1080 which uses as its light source either a single or multiple powered LEDs, LDs or SLEDs 1082. This light source provides light beam 1084 to anti-resonant waveguide 1086 in a manner as previously described. The fluorescing output light 1088 is directed toward an optic element 1090 and filter 1092 and finally to detector 1094, such as a CCD. Other detectors of course may be used, such as a photomultiplier tube, and the filters and other optics may or may not be required. In a typical implementation the optical element 1090 is used to image the fluorescence light onto the CCD array in order to enable a spatially resolved fluorescence signal. This way one can, for example, detect where on the biochip specific binding took place.

By use of system 1080, which can employ multiple LEDs LDs, SLEDs, multicolor excitation can easily be performed in a time sequential approach, or by parallel coupling of light sources. By using the LEDs LDs, SLEDs for excitation, the sequential approach can be done very easily since the light sources can be switched on and off quickly, in contrast to a conventionally used light source which usually needs long warm up times. For applications where very strong excitation is required, more light sources (e.g., LEDs, LDs, SLEDs) of the same type may be coupled in simultaneously. Again, since the excitation light is efficiently used and guided within the sample, a less demanding and therefore less expensive or even no detection filter may be required. This design, thus enables a simpler, more compact and less expensive system design both for single excitation and in the case of multicolor excitation.

Figure 29:
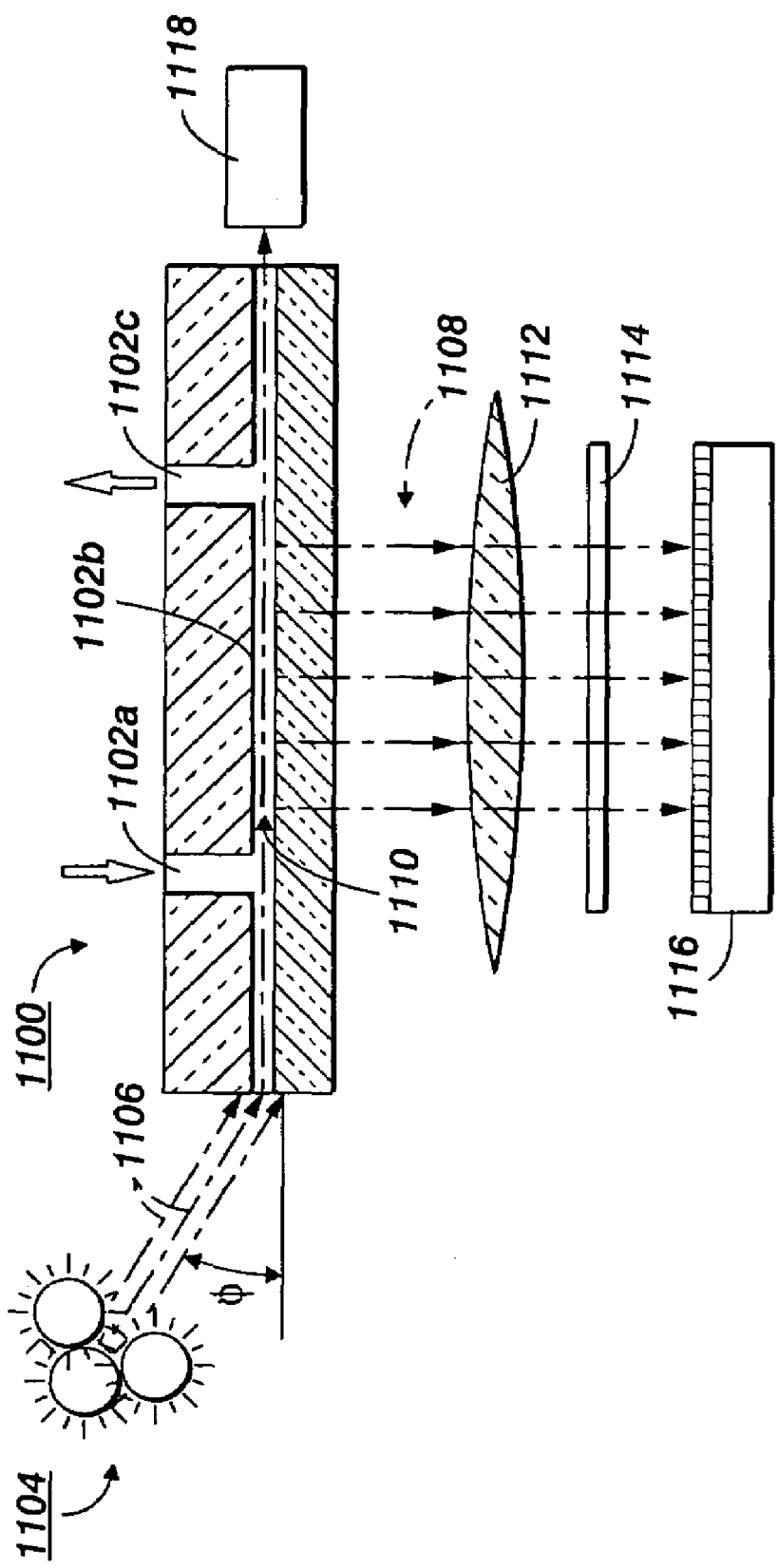
FIG. 29 is directed to a microfluidic excitation device.

The described excitation concepts implementing anti-resonant waveguide modes and smaller more compact light sources are particularly also useful in combination with microfluidic devices. For example, as shown in FIG. 29, a microfluidic device 1100 includes an input port 1102a, a fluidic channel 1102b and an output port 1102c. It is to be understood, the ports may come from the side of the device (i.e., perpendicular to the paper) in order to not interfere with the anti-resonant waveguide. A light source 1104, such as LEDs, LDs or SLEDs, generates light beam 1106 which is coupled to the microfluidic device 1100 in a manner as previously described, in order to generate fluorescing light 1108, from sample 1110. Provided to receive the output fluorescing light 1108 is an optics arrangement 1112, including a filter 1114 and a detector array 1116 used to determine lateral variations of fluorescence and/or scattering light, and/or a detector array 1118 for detecting light transmitted through the micro-fluidic device 1100. Again, various elements of this construction may or may not be required, depending on the particular application. In either case, FIG. 29 is intended to depict an embodiment where the excitation method using an anti-resonant waveguide is useful in combination with such microfluidic devices. As illustrated, microfluidic channels 1102b is used as the anti-resonant waveguide. It is to be appreciated FIG. 29 is a side view of microfluidic device 1100. Therefore, while a single microfluidic channel 1102b is shown, it is to be appreciated multiple channels and multiple inputs and outputs are part of such devices. By this design, efficient fluorescence excitation within the plurality of microfluidic channels is achieved. The readout of the fluorescence light is accomplished in a highly parallel manner, as in the above embodiment, with conventional optics and a detector such as the CCD camera.

The optical waveguide can be inline or perpendicular to the channels since thin walls between different channels will not result in disruption of the multiple optical waveguide configurations. By this design, multicolor excitation can be applied in a time sequential manner or by parallel launching of different light sources as illustrated, for example, in FIG. 8.

Figure 30:
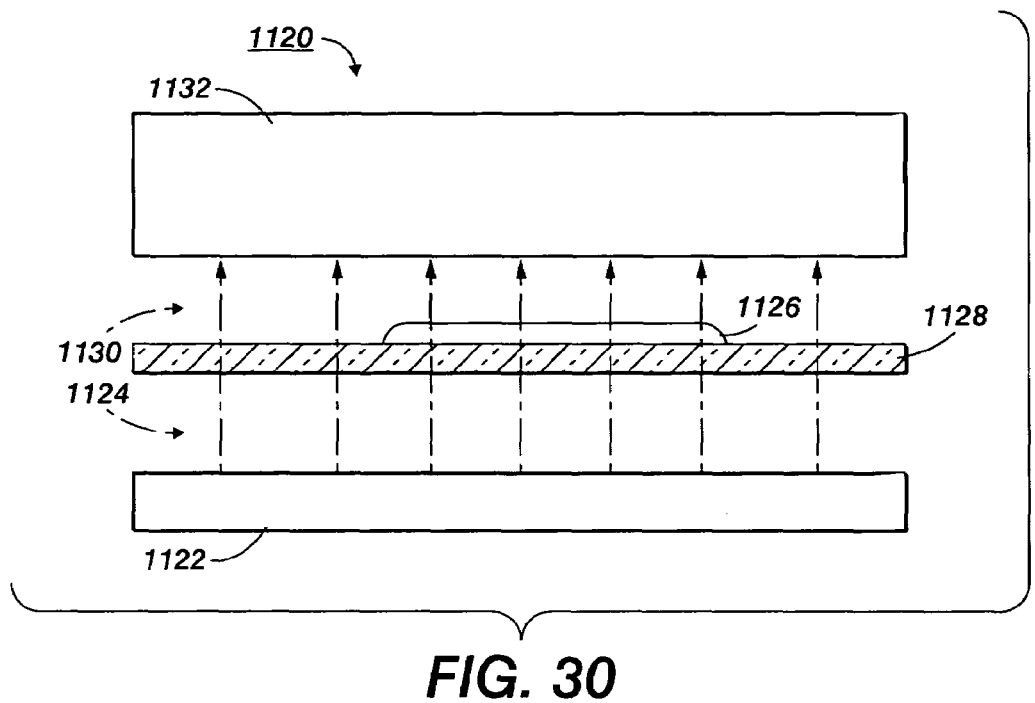
FIG. 30 depicts a biochip reader implementing a white light source.

Illustrating a particular implementation of the above concepts, attention is directed to FIG. 30, which shows an existing biochip reader 1120 including white light source 1122, such as a large halogen-type lamp 1122, to emit light beam 1124 for coupling to sample 1126. It is noted sample 1126 is not provided within an anti-resonant waveguide, but simply on a surface of substrate 1128. Fluorescing light 1130 is detected by a detector 1132, such as a CCD or other appropriate detector. In existing systems not employing the present concepts, it is usually necessary to employ expensive filters, not shown, to efficiently prevent the excitation light from entering the detector.

Figure 31:
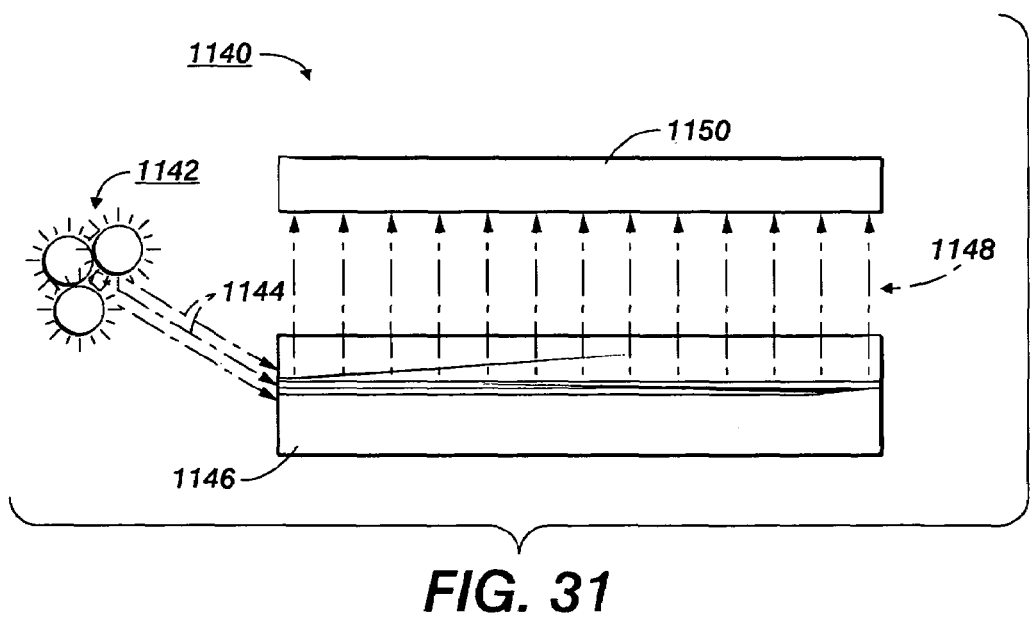
FIG. 31 shows a biochip reader implementing a light source in connection with the present concepts.

Using the concepts of the present application, biochip reader 1140 of FIG. 31 includes light source 1142, which is configured by a single or multiple LEDs, LDs or SLEDs. Light source 1142 emits light beam 1144 such that it is coupled to anti-resonant waveguide 1146 at a prescribed angle, and resulting emitted fluorescing light 1148 is detected by detector 1150. By implementation of the present concepts, the demand for filtering the fluorescence light is less stringent since the excitation light is guided within anti-resonant waveguide and only scattered light is contributing to the background.

As can be seen between FIGS. 30 and 31, a more compact, efficient detector is depicted in FIG. 31. The more compact device of FIG. 31 is achieved, since implementation of the anti-resonant waveguide concepts described herein permits the use of a light source that does not require the light intensity or power of a system not implementing the present anti-resonant waveguide concepts. It is to be appreciated the concepts described herein are also intended to represent readers or detectors, such as bio-sensors and detection applicable to electrophoresis processes.

Figure 32:
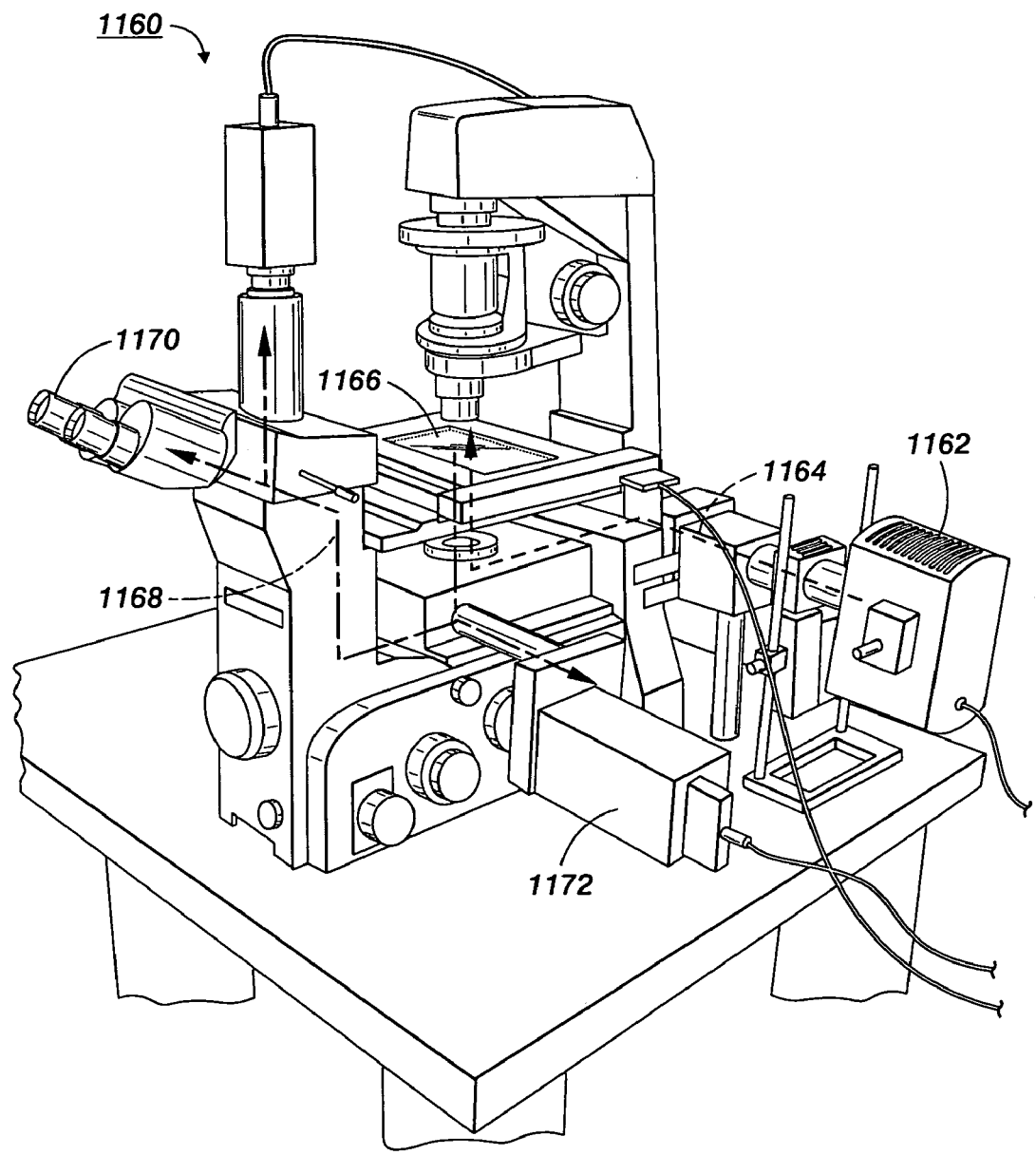
FIG. 32 depicts an existing fluorescent microscope.
Figure 33:
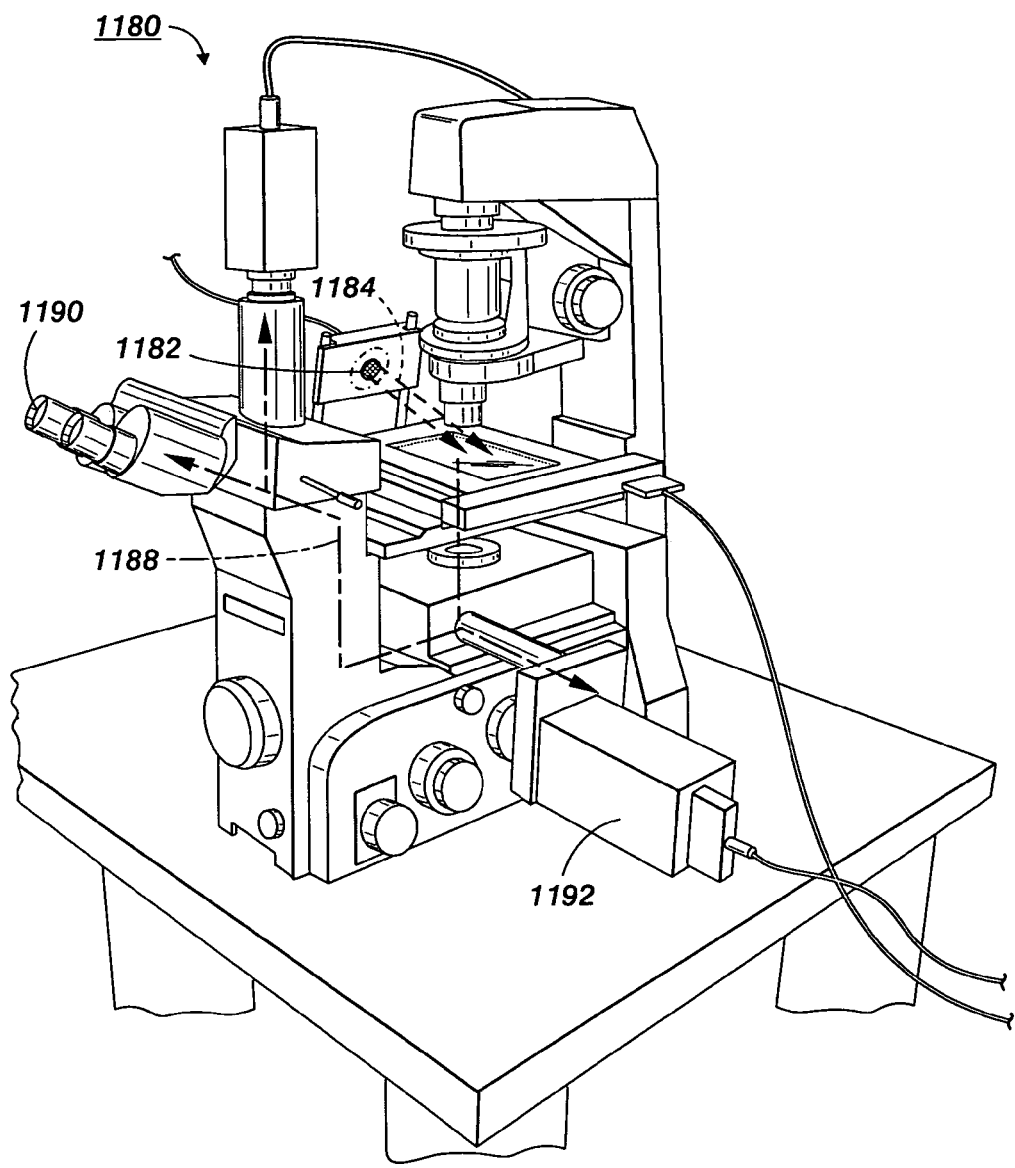
FIG. 33 depicts a fluorescent microscope implementing concepts of the present application.

With attention to another particular implementation, FIG. 32 depicts an existing (inverted) fluorescent microscope system 1160. A high pressure Hg arc lamp 1162 emits a light beam 1164, which is reflected in a path upward to cause fluorescing of a sample 1166. Fluorescing light from sample 1166 follows an emission light path 1168 providing the emitted light to detectors for a binocular arrangement 1170, and a camera 1172. As is clear from FIG. 32, high pressure Hg arc lamp 1162 takes up substantial space within the overall system 1160 (additional power supply is not shown). However, with attention to diagram of FIG. 33, an alternative fluorescence microscope system 1180 shows the high pressure Hg arc lamp 1162 (of FIG. 32) is replaced by an LED, LD and/or SLED light source 1182, positioned to provide light beam 1184 at a prescribed incident angle, to anti-resonant waveguide 1186 (not shown) in a manner previously described. The resulting fluorescing light 1186 from the sample of the waveguide follows emission light path 1188 to detectors of the binocular configuration 1190 and camera 1192 as in the previous design. The concepts of FIG. 33 clearly show that a much smaller, more compact electronic microscope may be obtained by using the light source 1182 and a waveguide (e.g., 1050) of the types as described herein. It is to be appreciated the described anti-resonant waveguide concepts can also be used in combination with conventional excitation sources as well.

Although optical detection techniques have been described, other methods of detecting the enhanced light-target interaction may be used. For example thermal detection techniques may be used. Predetermined light wavelengths may initiate a specific exothermic or endothermic chemical reaction which causes a temperature change. The detected temperature change indicates the presence of the reaction and thus the presence of compounds needed to create the reaction. Other example detection techniques include, but are not limited to, ARGOW induced photo ionization or photo fractionation. The photo ionization or photo fractionation generates charged particle which can be detected by known means such as a Coulter Counter.

In order to speed up analysis of the samples, parallel processing of a sample may occur. Thus the techniques described are not mutually exclusive and may be used in conjunction or in parallel to yield rapid detailed analysis of molecules in the sample.

The foregoing has been provided as examples to facilitate understanding of the invention, and to provide sample calculations. Further, while the foregoing examples have described the emitted light from the sample as fluorescing light, the output may be phosphorescence light or other output responsive to the cited excitation sources, or to other excitation sources, including but not limited to x-ray radiation or electron beam irradiation. However, the scope of the application should not be limited to these geometries or examples, nor the particular analysis techniques described. Instead, the concepts should only be limited by the claims, as originally presented and as they may be amended to encompass variations, alternatives, modifications, improvements, equivalents, and substantial equivalents of the embodiments and teachings disclosed herein, including those that are presently unforeseen or unappreciated, and that, for example, may arise from applicants/patentees and others.

The invention claimed is:

1. A sample detection system comprising:
   an anti-resonant waveguide including,
     a sample including a target analyte, the sample having a first index of refraction, and
     a top layer and a substrate surrounding the sample, the top layer having a second index of refraction and the substrate layer having a third index of refraction, the second index of refraction and the third index of refraction both greater than the first index of refraction;

a detection device including, a low power light source to direct light into the sample and generate an anti-resonant optical mode in the sample, an analyzing system to detect the interaction of the light propagating in the sample with the target analyte; and a light retention component configured with light reflective material to maintain light within the anti-resonant waveguide.

2. The system of claim 1, wherein the low power light source is a light source of approximately 700 mW or less.

3. The system of claim 1, wherein the light retention component is configured to surround at least three sides of the anti-resonant waveguide.

4. The system of claim 3, wherein the light retention component is configured to cover at least a portion of a side of the anti-resonant waveguide into which the light is directed.

5. The system of claim 1, wherein the light retention component is formed as part of the detection device.

6. The system of claim 1, wherein the light source is one of an LED, LD or SLD.

7. The system of claim 1, wherein the light source is a plurality of one of LEDs, LDs, or SLDs.

8. The system of claim 1, wherein the detection device is a fluorescence detection device.

9. The system of claim 1, wherein the detection device is a biochip reader.

10. The system of claim 1, wherein the detection device is a fluorescence microscope.

11. The system of claim 1, wherein the top layer and substrate are of differing lengths.

12. The system of claim 1, wherein the light source emits a plurality of wavelengths into the sample.

13. A sample detection system comprising:

an input area configured to receive a sample contained as part of an anti-resonant waveguide;

a light retention component configured with light reflective material to maintain light within the anti-resonant waveguide;

a lighting system arrangement positioned to emit light to a location within the input area, the location selected to reflect the light into the sample to operate the anti-resonant waveguide in an anti-resonant mode, the lighting system consisting of at least one diode; and an analyzing system positioned to detect the interaction of the light propagating in the sample.

14. The sample detector according to claim 13, wherein the diode is at least one of an LED, LD or SLD.

15. The sample detector of claim 13, wherein the light source is a plurality of one of LEDs, LDs, or SLDs.

16. The sample detector of claim 13, wherein the detection device is a fluorescence detecting device.

17. The sample detector of claim 13, wherein the detection device is a biochip reader.

18. The sample detector of claim 13, wherein the detection device is a fluorescence microscope.

19. The sample detector of claim 13, wherein the top layer and substrate are of differing lengths.

20. The sample detector of claim 13, wherein the light source emits a plurality of wavelengths into the sample.

21. A system to analyze a sample comprising:

a sample including a target analyte, the sample having a first index of refraction;

a top layer and a substrate surrounding the sample, one of the top layer or the substrate having a tilted end facet for receiving light, the top layer having a second index of refraction and the substrate having a third index of refraction, the second index of refraction and the third index of refraction both greater than the first index of refraction;

a light source to direct light into the sample via the tilted end facet and generate an anti-resonant guided optical mode in the sample;

an analyzing system to detect the interaction of the light propagating in the sample with the target analyte; and a light retention component configured with light reflective material to maintain light within the anti-resonant waveguide.

22. The system of claim 21, wherein one of the top layer or the substrate has a tilted end facet for receiving light.

* * * * *